(12) United States Patent
Tani et al.

(10) Patent No.: US 10,358,567 B2
(45) Date of Patent: Jul. 23, 2019

(54) COMPOUND, INK, INK CARTRIDGE AND INK JET RECORDING METHOD

(71) Applicant: CANON KABUSHIKI KAISHA, Tokyo (JP)

(72) Inventors: Yutaka Tani, Kawasaki (JP); Masanori Seki, Yokohama (JP); Yoshio Kinoshita, Tokyo (JP); Keigo Gouda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 176 days.

(21) Appl. No.: 15/442,500

(22) Filed: Feb. 24, 2017

(65) Prior Publication Data

US 2017/0247557 A1  Aug. 31, 2017

(30) Foreign Application Priority Data

Feb. 29, 2016  (JP) .................... 2016-038353
Jan. 27, 2017  (JP) .................... 2017-013676

(51) Int. Cl.
| | |
|---|---|
| *C09D 11/328* | (2014.01) |
| *C09D 11/037* | (2014.01) |
| *C09B 11/10* | (2006.01) |
| *C09B 11/12* | (2006.01) |
| *C07C 309/46* | (2006.01) |
| *C07C 309/58* | (2006.01) |

(52) U.S. Cl.
CPC .......... *C09D 11/328* (2013.01); *C07C 309/46* (2013.01); *C07C 309/58* (2013.01); *C09B 11/12* (2013.01); *C09D 11/037* (2013.01)

(58) Field of Classification Search
CPC ..... C09D 11/328; C09D 11/037; C09B 11/10; C09B 11/12; C07C 309/46; C07C 309/58
USPC .................................................. 106/31.43
See application file for complete search history.

(56) References Cited

U.S. PATENT DOCUMENTS

| | | | | | |
|---|---|---|---|---|---|
| 3,635,745 | A | * | 1/1972 | Rentel .................. | C09B 11/12 106/493 |
| 3,925,094 | A | * | 12/1975 | Papenfuss ............ | C09D 11/037 106/241 |
| 4,595,536 | A | * | 6/1986 | Hung ................... | C09B 11/10 552/111 |
| 5,198,558 | A | * | 3/1993 | Rines ................... | C09B 11/18 552/108 |
| 5,199,985 | A | * | 4/1993 | Schneider ............. | C09B 11/12 106/31.75 |
| 5,302,436 | A | * | 4/1994 | Miller .................. | B41M 5/5227 106/31.43 |
| 7,407,540 | B2 | * | 8/2008 | Yamagishi ........... | C09D 11/328 106/31.43 |
| 2005/0188894 | A1 | * | 9/2005 | Yamagishi ........... | C09D 11/328 106/31.43 |
| 2006/0234149 | A1 | * | 10/2006 | Toyoda ................ | C09B 11/24 430/108.21 |
| 2008/0045796 | A1 | * | 2/2008 | Yamamoto ........... | A61K 49/0023 600/160 |
| 2008/0281127 | A1 | * | 11/2008 | Kovi .................... | C07C 303/22 568/30 |
| 2009/0029120 | A1 | * | 1/2009 | Fujii .................... | C09D 11/40 106/31.47 |
| 2012/0013678 | A1 | * | 1/2012 | Yoneda ................ | C09D 11/328 106/31.13 |

FOREIGN PATENT DOCUMENTS

| | | | |
|---|---|---|---|
| DE | 2535215 | A1 * | 2/1977 |
| EP | 1528085 | A1 * | 5/2005 |
| JP | 46-4979 | | 11/1971 |
| JP | 2003-231834 | A | 8/2003 |
| JP | 2004-323605 | A | 11/2004 |
| WO | 2006/088170 | A1 | 8/2006 |
| WO | 2007/091631 | A1 | 8/2007 |
| WO | 2010/119676 | A1 | 10/2010 |

OTHER PUBLICATIONS

English translation of DE 2535215, Feb. 1977; 7 pages.*
Acid Blue 9 datasheet; http://www.worlddyevariety.com/acid-dyes/acid-blue-9.html, no date available; 8 pages.*

* cited by examiner

*Primary Examiner* — Helene Klemanski

(74) *Attorney, Agent, or Firm* — Canon U.S.A. Inc., IP Division

(57) ABSTRACT

A compound is represented by the following formula (1).

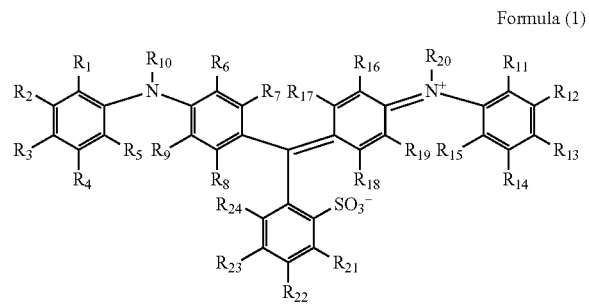

Formula (1)

In the compound represented by Formula (1), at least one of $R_1$ to $R_{24}$ is a group particularly high electron withdrawing property, such as a sulfonic acid group and a carboxylic acid group or a group having the next highest electron withdrawing property to the sulfonic acid group and the carboxylic acid group, such as a halogen atom.

13 Claims, 2 Drawing Sheets

COMPOUND, INK, INK CARTRIDGE AND INK JET RECORDING METHOD

BACKGROUND OF THE INVENTION

Field of the Invention

The present disclosure relates to a compound useful as a coloring material, an ink containing the compound, and the like.

Description of the Related Art

As a coloring material having a cyan hue and good color developability, a compound having a triphenylmethane skeleton is known. The compound having a triphenylmethane skeleton has good color developability because the compound has two high absorption bands (x-band and y-band) in a visible region and develops a visually recognized color tone by overlapping of complementary colors in the x-band on the long wavelength side and the y-band on the short wavelength side. Among the compounds having a triphenylmethane skeleton, C.I. Acid Blue 9 is widely known as a coloring material having a cyan hue and good color developability. Moreover, in order to improve the color developability of the compound having a triphenylmethane skeleton, an improvement of the structure has been performed (International Publication No. WO2006/088170 and Japanese Patent Laid-Open No. 46-004979).

Although the level demanded for the color developability and the fastness (ozone resistance, light fastness and moisture resistance) of the coloring material is increasing year after year, but the demand has not been able to be satisfied by the cyan coloring material. Compounds having a phthalocyanine skeleton are difficult to obtain the color developability comparable to those of the compounds having a triphenylmethane skeleton. The compounds described in International Publication No. WO2006/088170 and Japanese Patent Laid-Open No. 46-004979 have insufficient light fastness and ozone resistance.

SUMMARY OF THE INVENTION

The present disclosure provides a compound having high color developability and excellent also in ozone resistance, light fastness and moisture resistance and useful as a coloring material. The present disclosure also provides an ink containing the compound, an ink cartridge containing the ink and an ink jet recording method.

The above-described object is achieved according to the following disclosure. More specifically, a compound is represented by the following formula (1).

In Formula (1), $R_1$ to $R_{24}$ each independently represent a hydrogen atom, a halogen atom, an alkyl group, a cycloalkyl group, an alkenyl group, an alkynyl group, an aryl group, an aralkyl group, an acyl group, an acylamino group, a sulfonylamino group, an alkoxy group, an aryloxy group, a hydroxy group, an amino group, a nitro group, a cyano group, a sulfonic acid group, a carboxylic acid group, a sulfamoyl group, a carbamoyl group, an alkoxysulfonyl group, an alkoxycarbonyl group, an aryloxysulfonyl group or an aryloxycarbonyl group and satisfy at least one of the following (X) and (Y). (X) At least one of $R_1$ to $R_{24}$ is a sulfonic acid group or a carboxylic acid group. (Y) At least one of $R_6$, $R_7$, $R_8$, $R_9$, $R_{16}$, $R_{17}$, $R_{18}$ and $R_{19}$ is a halogen atom, an acyl group, a nitro group or a cyano group.

Further features of the disclosure will become apparent from the following description of exemplary embodiments with reference to the attached drawings.

DESCRIPTION OF THE EMBODIMENTS

Figure 1:
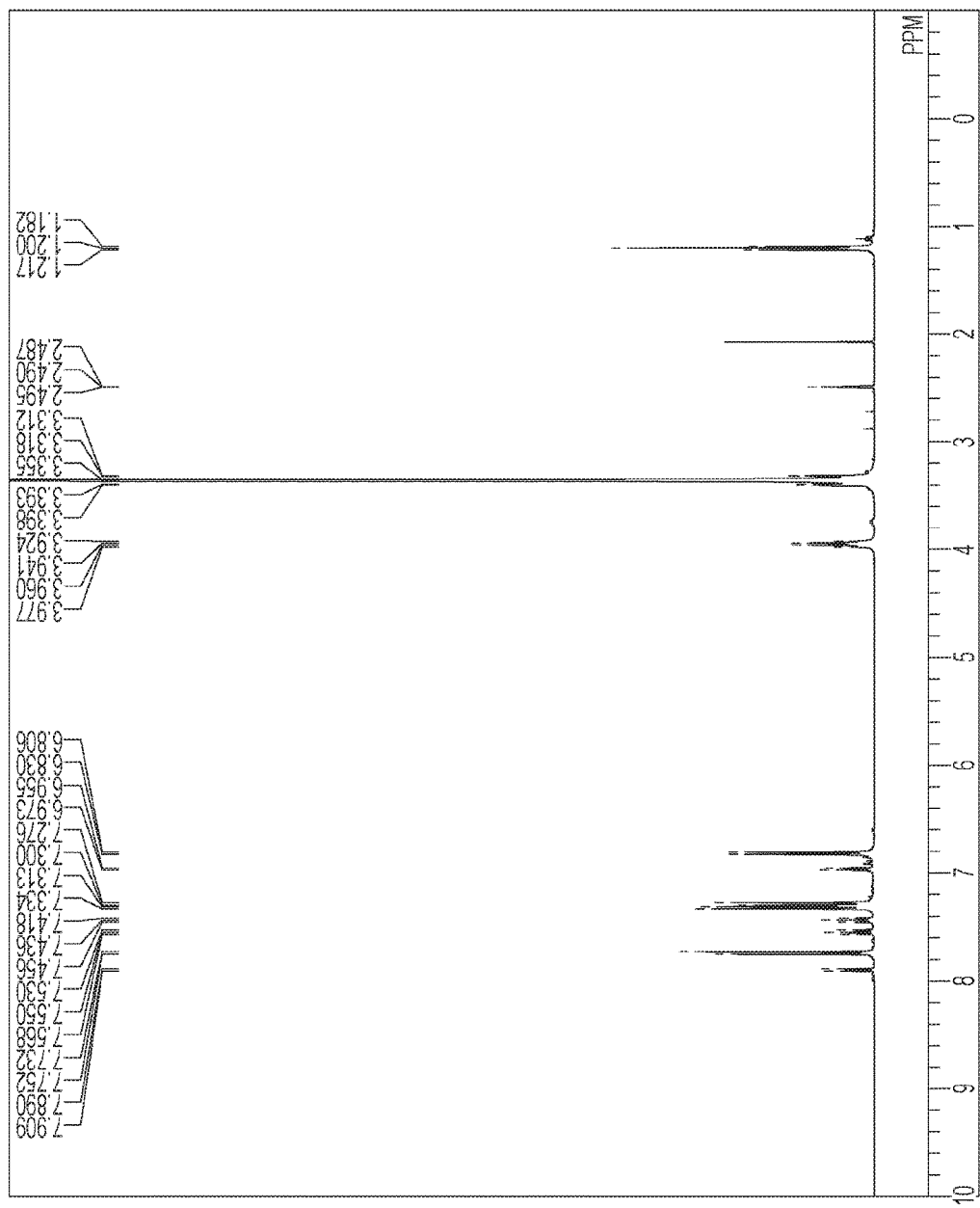
FIG. 1 is a chart showing the $^1$H-NMR analysis results of Exemplified Compound 14.

Hereinafter, the present disclosure is described in more detail with reference to a preferable embodiment. In the present disclosure, when the compound is a salt, at least a part of the salt may be present in a state of being dissociated into ions in water or an aqueous liquid, such as ink, but the compound is referred to as "salt" for convenience.

Compound Represented by Formula (1)

As a result of an examination, the present inventors have found a compound represented by the following formula (1) as a compound having high color developability and excellent in ozone resistance, light fastness and moisture resistance. The compound represented by Formula (1) is one in which a benzene ring is bonded to both sides of the triphenylmethane skeleton through an imino group and which satisfies at least one of the following (X) and (Y). (X) At least one of $R_1$ to $R_{24}$ is a sulfonic acid group or a carboxylic acid group. (Y) At least one of $R_6$, $R_7$, $R_8$, $R_9$, $R_{16}$, $R_{17}$, $R_{18}$ and $R_{19}$ is a halogen atom, an acyl group, a nitro group or a cyano group. The compound satisfies at least one of (X) and (Y) above, i.e., a group having an electron withdrawing group is substituted at a specific position, and therefore the

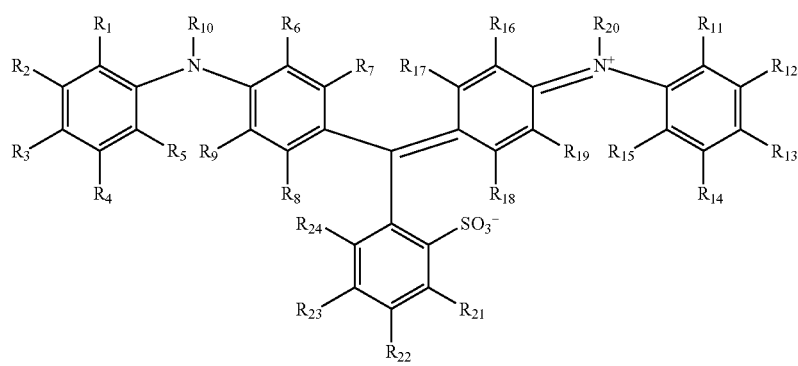

Formula (1)

compound has high color developability and is excellent in ozone resistance, light fastness and moisture resistance.

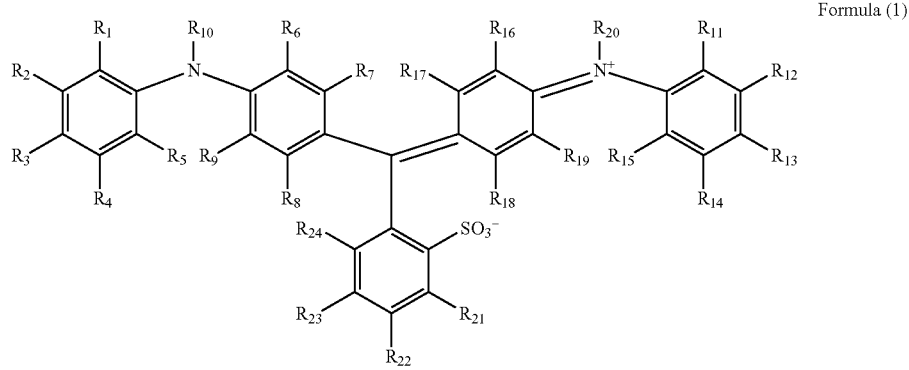

Formula (1)

In Formula (1), $R_1$ to $R_{24}$ each independently represent a hydrogen atom, a halogen atom, an alkyl group, a cycloalkyl group, an alkenyl group, an alkynyl group, an aryl group, an aralkyl group, an acyl group, an acylamino group, a sulfonylamino group, an alkoxy group, an aryloxy group, a hydroxy group, an amino group, a nitro group, a cyano group, a sulfonic acid group, a carboxylic acid group, a sulfamoyl group, a carbamoyl group, an alkoxysulfonyl group, an alkoxycarbonyl group, an aryloxysulfonyl group or an aryloxycarbonyl group and satisfy at least one of the following (X) and (Y). (X) At least one of $R_1$ to $R_{24}$ is a sulfonic acid group or a carboxylic acid group. (Y) At least one of $R_6$, $R_7$, $R_8$, $R_9$, $R_{16}$, $R_{17}$, $R_{18}$ and $R_{19}$ is a halogen atom, an acyl group, a nitro group or a cyano group.

The triphenylmethane skeleton is a portion surrounded by the dotted line in the following figure. The following description is given on the premise that two benzene rings located in the upper side of the triphenylmethane skeleton are referred to as A rings, two benzene rings located on both outsides of the triphenylmethane skeleton are referred to as B rings, and a benzene ring located on the lower side of the triphenylmethane skeleton is referred to as a C ring. The ortho position and the meta position about the B rings are shown as the positions based on an imino group bonded to the triphenylmethane skeleton.

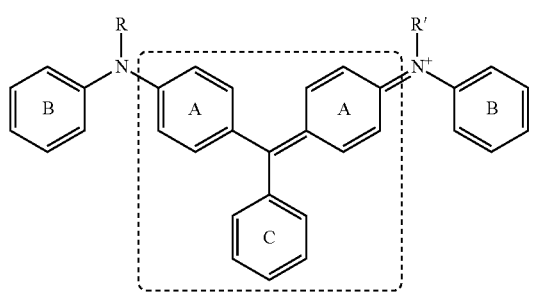

In Formula (1), $R_1$ to $R_{24}$ each independently represent a hydrogen atom, a halogen atom, an alkyl group, a cycloalkyl group, an alkenyl group, an alkynyl group, an aryl group, an aralkyl group, an acyl group, an acylamino group, a sulfonylamino group, an alkoxy group, an aryloxy group, a hydroxy group, an amino group, a nitro group, a cyano group, a sulfonic acid group, a carboxylic acid group, a sulfamoyl group, a carbamoyl group, an alkoxysulfonyl group, an alkoxycarbonyl group, an aryloxysulfonyl group or an aryloxycarbonyl group. $R_1$ to $R_{24}$ satisfy at least one of the following (X) and (Y). (X) At least one of $R_1$ to $R_{24}$ is a sulfonic acid group or a carboxylic acid group. (Y) At least one of $R_6$, $R_7$, $R_8$, $R_9$, $R_{16}$, $R_{17}$, $R_{18}$ and $R_{19}$ is a halogen atom, an acyl group, a nitro group or a cyano group.

Examples of the halogen atom include a fluorine atom, a chlorine atom, a bromine atom, an iodine atom, and the like, for example.

Examples of the alkyl group include a straight or branched chain alkyl group having 1 to 12 carbon atoms. The alkyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkoxy groups having 1 to 6 carbon atoms, such as a methoxy group, an ethoxy group, a propoxy group and a butoxy group; a hydroxy group; an amino group; a cyano group; a sulfonic acid group; a carboxylic acid group; and the like. Examples of the alkyl group include, when those having a substituent are included, unsubstituted alkyl groups, such as a methyl group, an ethyl group, a propyl group, an isopropyl group, a butyl group, an isobutyl group, a sec-butyl group, a tert-butyl group, a pentyl group, an isopentyl group, a sec-pentyl group, a tert-pentyl group, a neopentyl group, a hexyl group, a heptyl group, an octyl group, a 2-ethylhexyl group and a dodecyl group; substituted alkyl groups, such as a trifluoromethyl group, a 2-methoxyethyl group, a 1-hydroxyethyl group, a 1-aminoethyl group, a 2-cyanoethyl group, a 3-sulfopropyl group and a 3-carboxypropyl group, for example.

Examples of the cycloalkyl group include a monocyclic or bicyclic cycloalkyl group having 3 to 12 carbon atoms. The cycloalkyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a cyano group; a sulfonic acid group; a carboxylic acid group; and the like. Examples of the cycloalkyl group include, when those having a substituent are included, unsubstituted cycloalkyl groups, such as a cyclopropyl group, a cyclobutyl group, a cyclopentyl group, a cyclohexyl group, a cycloheptyl group, a cyclooctyl group, a decahydronaphthyl group, an adamantyl group and a dodecahydroacenaphthylenyl group; and substituted cyclohexyl groups, such as a 2-chlorocyclohexyl group, a 2-methylcyclohexyl group, a 3-methylcyclohexyl group, a 4-methylcyclohexyl group, a 2,6-dimethylcyclohexyl group, a 2,4,6-trimethylcyclohexyl group, a 4-methoxycyclohexyl group, a 2-hydroxycyclohexyl group, a 2-aminocyclohexyl group, a 3-cyanocyclohexyl group, a 3-sulfocyclohexyl group and a 2-carboxycyclohexyl group, for example.

Examples of the alkenyl group include a straight or branched chain alkenyl group having 2 to 12 carbon atoms. Examples of the alkenyl group include, for example, a vinyl group, a 1-propenyl group, a 2-propenyl group, a 1-methylethenyl group, a 1-butenyl group, a 2-butenyl group, a 3-butenyl group, a 1-hexenyl group, a 1-dodecenyl group, and the like.

Examples of the alkynyl group include a straight or branched chain alkynyl group having 2 to 12 carbon atoms. Examples of the alkynyl group include, for example, an ethynyl group, a 2-propynyl group, a 1-butynyl group, a 1-hexynyl group, a 1-dodecenyl group, and the like.

Examples of the aryl group include an aryl group of having 6 to 10 carbon atoms. The aryl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a cyano group; a sulfonic acid group; a carboxylic acid group; and the like. Examples of the aryl group include, when those having a substituent are included, unsubstituted aryl groups, such as a phenyl group, a 1-naphthyl group and a 2-naphthyl group; and substituted aryl groups, such as an o-chlorophenyl group, an o-tolyl group, a m-tolyl group, a p-tolyl group, a 2,6-dimethylphenyl group, a 2,4,6-trimethylphenyl group, a p-methoxyphenyl group, an o-aminophenyl group, an o-hydroxyphenyl group, a m-cyanophenyl group, a m-sulfophenyl group, an o-carboxyphenyl group, a 2-hydroxy-1-naphthyl group and a 1-hydroxy-2-naphthyl group, for example.

Examples of the aralkyl group include an aralkyl group having 7 to 12 carbon atoms. The aralkyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a nitro group; a sulfonic acid group; a carboxylic acid group; and the like. Examples of the aralkyl group include, when those containing a substituent are included, unsubstituted aralkyl groups, such as a benzyl group, a 2-phenethyl group and a 2-(1-naphthyl)ethyl group; and substituted aralkyl groups, such as a 4-bromobenzyl group, a 2-(3-fluorophenyl)ethyl group, a 2-methylbenzyl group, a 3,5-dimethoxybenzyl group, a 3,5-dihydroxybenzyl group, a 2-nitrobenzyl group, a 3-sulfobenzyl group, 2-carboxybenzyl group and a 3-carboxybenzyl group, for example.

Examples of the acyl group include a straight or branched chain hydrocarbon-based acyl group having 1 to 12 carbon atoms and an aromatic acyl group having 7 to 13 carbon atoms. The acyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkoxy groups having 1 to 6 carbon atoms, such as a methoxy group, an ethoxy group, a propoxy group and a butoxy group; a hydroxy group; a nitro group; a cyano group; a sulfonic acid group; a carboxylic acid group; and the like. Examples of the acyl group include, when those containing a substituent are included, unsubstituted acyl groups, such as a methanoyl group, an ethanoyl group, a propanoyl group, a butanoyl group, an isobutanoyl group, a pentanoyl group, a hexanoyl group, a dodecanoyl group, a propenoyl group, a 2-methylpropenoyl group, a benzoyl group and a 2-naphthoyl group; and substituted acyl groups, such as a 2,2,2-trifluoroethanoyl group, a 2,2-dimethoxyethanoyl group, a 2-hydroxyethanoyl group, a 2-nitroethanoyl group, a 2-cyanoethanoyl group, a 3-carboxypropanoyl group and a 2-sulfobenzoyl group, for example.

Examples of the acylamino group include a straight or branched chain hydrocarbon-based acylamino group having 1 to 12 carbon atoms and an aromatic acylamino group having 7 to 12 carbon atoms. The acylamino group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkoxy groups having 1 to 6 carbon atoms, such as a methoxy group, an ethoxy group, a propoxy group and a butoxy group; a hydroxy group; an amino group; a nitro group; a cyano group; a sulfonic acid group; a carboxylic acid group; a group obtained by combining at least two kinds thereof, and the like. Examples of the acylamino group include, when those having a substituent are included, unsubstituted acylamino groups, such as a methanoylamino group, an ethanoylamino group, a propanoylamino group, a butanoylamino group, an isobutanoylamino group, a pentanoylamino group, a hexanoylamino group, a dodecanoylamino group, a propenoylamino group, a 2-methylpropenoylamino group, a benzoylamino group, a phthalimidyl group, a 2-naphthoylamino group and a dibenzoylamino group; substituted acylamino groups, such as a 2,2,2-trifluoroethanoylamino group, a 2,2-dimethoxyethanoylamino group, a 2-hydroxyethanoylamino group, a 2-aminobutanoylamino group, a 2-nitroethanoylamino group, a 2-cyanoethanoylamino group, a 3-carboxypropanoylamino group, a 2-sulfobenzoylamino group and a 2-carboxybenzoylamino group, for example.

Examples of the sulfonylamino group include a straight or branched chain hydrocarbon-based sulfonylamino group having 1 to 12 carbon atoms and an aromatic sulfonylamino group having 6 to 10 carbon atoms. The sulfonylamino group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom, alkoxy groups having 1 to 6 carbon atoms, such as a methoxy group, an ethoxy group, a propoxy group and a butoxy group; a hydroxy group; an amino group; a nitro group; a cyano group; a sulfonic acid group; a carboxylic acid group; a group obtained by combining at least two kinds thereof; and the like. Examples of the sulfonylamino group include, when those having a substituent are included, unsubstituted hydrocarbon-based and aromatic sulfonylamino groups, such as a methanesulfonylamino group, an ethanesulfonylamino group, a propanesulfonylamino group, a butanesulfonylamino group, an isobutanesulfonylamino group, pentanesulfonylamino amino group, a hexanesulfonylamino group, a dodecanesulfonylamino group, a propensulfonylamino group, a 2-methylpropensulfonylamino group, a phenylmethanesulfonylamino group, a p-toluenesulfonylamino group and a 1-naphthalenesulfonylamino group; and hydrocarbon-based and aromatic sulfonylamino groups having a substituent, such as a trifluoromethanesulfonylamino group, a dimethoxymethanesulfonylamino group, 2-hydroxymethanesulfonylamino group, a 2-aminoethanesulfonylamino group, a 2-nitroethanesulfonylamino group, a 2-cyanoethanesulfonylamino group, a 3-carboxypropanesulfonylamino group and a 2-sulfophenylmethanesulfonylamino group, for example.

Examples of the alkoxy group include a straight or branched chain alkoxy group having 1 to 12 carbon atoms. The alkoxy group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a nitro group; a sulfonic acid group; a carboxylic acid group; a group obtained by combining at least two kinds thereof; and the like. The alkoxy group include, when those containing a substituent are included, unsubstituted alkoxy groups, such as a methoxy group, an ethoxy group, a propoxy group, an isopropoxy group, a butoxy group, a tert-butoxy group, a pentyloxy group, a hexyloxy group, a heptyloxy group, an octyloxy group, 2-ethylhexyloxy group and a dodecyloxy group; and substituted alkoxy groups, such as a 2-methylethoxy group, a 2-chloroethoxy group, a methoxy methoxy group, a 3-hydroxypropoxy group, a 4-dimethylaminobutoxy group, a 3-sulfopropoxy group and a 3-carboxymethoxy group, for example.

Examples of the aryloxy group include an aryloxy group having 6 to 10 carbon atoms. The aryloxy group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a cyano group; a sulfonic acid group; a carboxylic acid group; and the like. Examples of the aryloxy group include, when those having a substituent are included, unsubstituted aryloxy groups, such as a phenoxy group, 1-naphthoxy group and 2-naphthoxy group; and substituted aryloxy groups, such as an o-chlorophenoxy group, an o-methylphenoxy group, a m-methylphenoxy group, a p-methylphenoxy group, a 2,6-dimethylphenoxy group, a 2,4,6-trimethylphenoxy group, a p-methoxyphenoxy group, an o-hydroxyphenoxy group, a 2-hydroxy-1-naphthoxy group, a 1-hydroxy-2-naphthoxy group, a m-aminophenoxy group, a m-cyanophenoxy group, a m-sulfophenoxy group and an o-carboxyphenoxy group, for example.

Examples of the amino group include a non-substituted amino group and a substituted amino group. The substituent can be selected as long as the color developability, the ozone resistance, the light fastness and the moisture resistance of the compound represented by Formula (1) are not impaired. Examples of such a substituent include, for example, alkyl groups having 1 to 12 carbon atoms, such as a methyl group, an ethyl group, a propyl group, an isopropyl group, a butyl group, a tert-butyl group and a dodecyl group; alkenyl groups having 2 to 12 carbon atoms, such as a vinyl group, a 1-propenyl group, a 2-propenyl group, a 1-butenyl group, a 2-butenyl group and a 1-dodecenyl group; aryl groups having 6 to 10 carbon atoms, such as a phenyl group, a 1-naphthyl group and a 2-naphthyl group; aralkyl groups having 7 to 12 carbon atoms, such as a benzyl group, a 2-phenethyl group and a 2-(1-naphthyl)ethyl group; a sulfonic acid group; a carboxylic acid group; and the like. These substituents may further have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkoxy groups having 1 to 6 carbon atoms, such as a methoxy group, an ethoxy group, a propoxy group and a butoxy group; a hydroxy group; a nitro group; a cyano group; a sulfonic acid group; a carboxylic acid group; and the like. Examples of the substituted amino group include, for example, a methylamino group, a dimethylamino group, a diethylamino group, a dibutylamino group, a 2-ethylhexylamino group, a dodecylamino group, a 2,2,2-trifluoroethylamino group, a 2,2-dimethoxyethylamino group, a 2-hydroxyethylamino group, a 2-nitroethylamino group, a 2-cyanoethyl group, a 2-sulfoethylamino group, a 2-carboxyethylamino group, a vinylamino group, a 2-propenylamino group, an anilino group, a diphenylamino group, a benzylamino group, an N-sulfamic acid group, an N-carbamic acid group, and the like.

The sulfonic acid group and the carboxylic acid group may be either an acid type or a salt type. However, in the case of a salt type, at least a part of the groups may be ionically dissociated in an aqueous ink to generate counterions. However, the groups are referred to as "salt type sulfonic acid group or a salt type carboxylic acid group" in this specification for convenience. Examples of the counterions forming salts include, for example, ions of alkali metals, such as lithium, sodium and potassium; unsubstituted ammonium; organic ammonium, such as methylammonium, dimethylammonium, trimethylammonium, tetramethylammonium, ethylammonium, diethylammonium, triethylammonium, tetraethylammonium, n-propylammonium, isopropylammonium, diisopropylammonium, n-butylammonium, tetra n-butylammonium, isobutylammonium, monoethanol ammonium, diethanol ammonium and triethanol ammonium; pyridinium, such as N-methyl pyridinium; imidazolium, such as 1-ethyl-3-methyl imidazolium; phosphonium, such as tetra n-butyl phosphonium; sulfonium, such as tri n-butyl sulfonium; and the like. When using the compound of the present disclosure as a coloring material of an aqueous ink, it is preferable that the compound represented by Formula (1) has at least one of the sulfonic acid group and the carboxylic acid group.

Not only the sulfonic acid group and the carboxylic acid group as $R_1$ to $R_{24}$ but anionic groups, such as a sulfonic acid group and a carboxylic acid group, which $R_1$ to $R_{24}$ may have as a substituent, may be either an acid type or a salt type. For example, examples of counterions in the case of a salt type anionic group include the same counterions as the counterions mentioned above.

Examples of the sulfamoyl group include an unsubstituted sulfamoyl group (aminosulfonyl group) and a substituted sulfamoyl group. The substituents can be selected as long as the color developability, the ozone resistance, the light fastness and the moisture resistance of the compound represented by Formula (1) are not impaired. Examples of such a substituent include, for example, alkyl groups having 1 to 12 carbon atoms, such as a methyl group, an ethyl group, a propyl group, an isopropyl group, a butyl group, a tert-butyl group and a dodecyl group; alkenyl groups having 2 to 12 carbon atoms, such as a vinyl group, a 1-propenyl group, a 2-propenyl group, a 1-butenyl group, a 2-butenyl group and a 1-dodecenyl group; aryl groups having 6 to 10 carbon atoms, such as a phenyl group and a 2-naphthyl group; aralkyl groups having 7 to 12 carbon atoms, such as a benzyl group, a 2-phenethyl group and a 2-(1-naphthyl)ethyl group; and the like. These substituents may further have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkoxy groups having 1 to 6 carbon atoms, such as a methoxy group, an ethoxy group, a propoxy group and a butoxy group; a hydroxy group; a sulfonic acid group; a carboxylic acid group; and the like. Examples of the substituted sulfamoyl group include, for example, a methylaminosulfonyl group, a dimethylaminosulfonyl group, an ethylaminosulfonyl group, a propylaminosulfonyl group, an isopropylaminosulfonyl group, a butylaminosulfonyl group, an isobutylaminosulfonyl group, a tert-butylaminosulfonyl group, a pentylaminosulfonyl group, a hexylaminosulfonyl group, a heptylaminosulfonyl group, an octylaminosulfonyl group, a 2-ethylhexylaminosulfonyl group, a dodecylaminosulfonyl group, a 2,2,2-trifluoroethylaminosulfonyl group, a 2,2-dimethoxyethylaminosulfonyl group, a 2-hydroxyethylaminosulfonyl group, a 2-sulfoethylaminosulfonyl group, a 2-carboxyethylaminosulfonyl group, a vinylaminosulfonyl group, a 2-propenylaminosulfonyl group, an anilinosulfonyl group and a diphenylaminosulfonyl group.

Examples of the carbamoyl group include an unsubstituted carbamoyl group (aminocarbonyl group) and a substituted carbamoyl group. The substituents can be selected as long as the color developability, the ozone resistance, the light fastness and the moisture resistance of the compound represented by Formula (1) are not impaired. Examples of such a substituent include, for example, alkyl groups having 1 to 12 carbon atoms, such as a methyl group, an ethyl group, a propyl group, an isopropyl group, a butyl group, a tert-butyl group and a dodecyl group; alkenyl groups having 2 to 12 carbon atoms, such as a vinyl group, a 1-propenyl group, a 2-propenyl group, a 1-butenyl group, a 2-butenyl group and a 1-dodecenyl group; aryl groups having 6 to 10 carbon atoms, such as a phenyl group and a naphthyl group; aralkyl groups having 7 to 12 carbon atoms, such as a benzyl group, a 2-phenethyl group and a 2-(1-naphthyl)ethyl group; and the like. These substituents may further have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkoxy groups having 1 to 6 carbon atoms, such as a methoxy group, an ethoxy group, a propoxy group and a butoxy group; a hydroxy group; a sulfonic acid group; a carboxylic acid group; and the like. Examples of the substituted carbamoyl group include, for example, a methylaminocarbonyl group, a dimethylaminocarbonyl group, an ethylaminocarbonyl group, a propylaminocarbonyl group, an isopropylaminocarbonyl group, a butylaminocarbonyl group, an isobutylaminocarbonyl group, a tert-butylaminocarbonyl group, a pentylaminocarbonyl group, a hexylaminocarbonyl group, a heptylaminocarbonyl group, an octylaminocarbonyl group, a 2-ethylhexylaminocarbonyl group, a dodecylaminocarbonyl group, a 2,2,2-trifluoroethylaminocarbonyl group, a 2,2-dimethoxyethylaminocarbonyl group, a 2-hydroxyethylaminocarbonyl group, a 2-sulfoethylaminocarbonyl group, a 2-carboxyethylaminocarbonyl group, a vinylaminocarbonyl group, a 2-propenylaminocarbonyl group, an anilinocarbonyl group, a diphenylaminocarbonyl group, and the like.

Examples of the alkoxysulfonyl group include a straight or branched chain alkoxysulfonyl group having 1 to 12 carbon atoms. The alkoxysulfonyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a sulfonic acid group; a carboxylic acid group; a group obtained by combining at least two kinds thereof; and the like. Examples of the alkoxysulfonyl group include, when those having a substituent are included, unsubstituted alkoxysulfonyl groups, such as a methoxysulfonyl group, an ethoxysulfonyl group, a propoxysulfonyl group, an isopropoxysulfonyl group, a butoxysulfonyl group, an isobutoxysulfonyl group, a tert-butoxysulfonyl group, a pentyloxysulfonyl group, a hexyloxysulfonyl group, a heptyloxysulfonyl group, an octyloxysulfonyl group, a 2-ethylhexyloxysulfonyl group and a dodecyloxysulfonyl group; and substituted alkoxysulfonyl groups, such as a 2-methylethoxysulfonyl group, a 2-chloroethoxysulfonyl group, a methoxymethoxysulfonyl group, a 3-hydroxypropoxysulfonyl group, a 4-dimethylaminobutoxysulfonyl group, a 3-sulfopropoxysulfonyl group and a carboxymethoxysulfonyl group, for example.

Examples of the alkoxycarbonyl group include a straight or branched chain alkoxycarbonyl group having 2 to 12 carbon atoms. The alkoxycarbonyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a sulfonic acid group; a carboxylic acid group; a group obtained by combining at least two kinds thereof; and the like. Examples of the alkoxycarbonyl group include, when those having a substituent are included, unsubstituted alkoxycarbonyl groups, such as a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, a hexyloxycarbonyl group, a heptyloxycarbonyl group, an octyloxycarbonyl group, a 2-ethylhexyloxycarbonyl group and a dodecyloxycarbonyl group; and substituted alkoxycarbonyl groups, such as a 2-methylethoxycarbonyl group, a 2-chloroethoxycarbonyl group, a methoxymethoxycarbonyl group, a 3-hydroxypropoxycarbonyl group, a 4-dimethylaminobutoxycarbonyl group, a 3-sulfopropoxycarbonyl group and a carboxymethoxycarbonyl group, for example.

Examples of the aryloxysulfonyl group include an aryloxysulfonyl group having 6 to 10 carbon atoms. The aryloxysulfonyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a cyano group; a sulfonic acid group; a carboxylic acid group; and the like. Examples of the aryloxysulfonyl group include, when those having a substituent are included, unsubstituted aryloxysulfonyl groups, such as a phenoxysulfonyl group and a 1-naphthoxysulfonyl group; and substituted aryloxysulfonyl groups, such as an o-chlorophenoxysulfonyl group, an o-methylphenoxysulfonyl group, a m-methylphenoxysulfonyl group, a p-methylphenoxysulfonyl group, a 2,6-dimethylphenoxysulfonyl group, a 2,4,6-trimethylphenoxysulfonyl group, a p-methoxyphenoxysulfonyl group, an o-hydroxyphenoxysulfonyl group, a 2-hydroxy-1-naphthoxysulfonyl group, a 1-hydroxy-2-naphthoxysulfonyl group, an o-aminophenoxysulfonyl group, a m-cyanophenoxysulfonyl group, a m-sulfophenoxysulfonyl group and an o-carboxyphenoxysulfonyl group, for example.

Examples of the aryloxycarbonyl group include an aryloxycarbonyl group having 7 to 12 carbon atoms. The aryloxycarbonyl group may have a substituent as long as the color developability, the ozone resistance, the light fastness and the moisture resistance of the compound represented by Formula (1) are not impaired. Examples of such a substituent include, for example, halogen atoms, such as a fluorine atom, a chlorine atom and a bromine atom; alkyl groups having 1 to 6 carbon atoms, such as a methyl group, an ethyl group, a propyl group, an isopropyl group, a butyl group and a tert-butyl group; alkoxy groups having 1 to 6 carbon atoms, such as a methoxy group, an ethoxy group, a propoxy group and a butoxy group; a hydroxy group; an amino group; a cyano group; a sulfonic acid group; a carboxylic acid group; and the like. Examples of the aryloxycarbonyl group include, when those having a substituent are included, unsubstituted aryloxycarbonyl groups, such as a phenoxycarbonyl group and a 1-naphthoxycarbonyl group; and substituted aryloxycarbonyl groups, such as an o-chlorophenoxycarbonyl group, an o-methylphenoxycarbonyl group, a m-methylphenoxycarbonyl group, a p-methylphenoxycarbonyl group, a 2,6-dimethylphenoxycarbonyl group, a 2,4,6-trimethylphenoxycarbonyl group, a p-methoxyphenoxycarbonyl group, an o-hydroxyphenoxycarbonyl group, a 2-hydroxy-1-naphthoxycarbonyl group, a 1-hydroxy-2-naphthoxycarbonyl group, an o-aminophenoxycarbonyl group, a m-cyanophenoxycarbonyl group, a m-sulfophenoxycarbonyl group and an o-carboxyphenoxycarbonyl group, for example.

When (X) and (Y) are not satisfied in Formula (1), the effect of simultaneously improving all of the ozone resistance, the light fastness and the moisture resistance while having high color developability cannot be obtained. In order to obtain the effect of the present disclosure, a group having particularly high electron withdrawing property, such as a sulfonic acid group and a carboxylic acid group, need to be directly bonded to the skeleton of a coloring material or a group having the next highest electron withdrawing property to the sulfonic acid group and the carboxylic acid group, such as a halogen atom, need to be directly bonded to the A rings.

Since more excellent ozone resistance is obtained, it is preferable to select a group having high electron withdrawing property as a group directly bonded to the triphenylmethane skeleton. Therefore, the number of $R_1$ to $R_{24}$ in Formula (1) which represent a halogen atom, an acyl group, a nitro group, a cyano group, a sulfonic acid group and a carboxylic acid group is preferably 2 or more to 5 or less. It is effective for the improvement of the ozone resistance to select a group having high electron withdrawing property as a group directly bonded to the triphenylmethane skeleton. Therefore, the number does not include the substituent mentioned above as the substituent which the groups represented by $R_1$ to $R_{24}$ further have.

Since more excellent ozone resistance is obtained, it is preferable to select a group having high electron withdrawing property as a group directly bonded to the A rings. Therefore, it is preferable that at least one of $R_6$, $R_7$, $R_8$, $R_9$, $R_{16}$, $R_{17}$, $R_{18}$ and $R_{19}$ in Formula (1) is a halogen atom, an acyl group, a nitro group, a cyano group, a sulfonic acid group or a carboxylic acid group. In particular, since particularly excellent ozone resistance is obtained, it is preferable to select a group having high electron withdrawing property as a group directly bonded to the A rings. Therefore, at least one of $R_6$, $R_7$, $R_8$, $R_9$, $R_{16}$, $R_{17}$, $R_{18}$ and $R_{19}$ in Formula (1) is more preferably a sulfonic acid group or a carboxylic acid group.

Since more excellent light fastness and moisture resistance are obtained, it is preferable that groups having a plurality of electron donating property are present in the B rings. Therefore, it is preferable that at least two of $R_1$, $R_2$, $R_3$, $R_4$, $R_5$, $R_{11}$, $R_{12}$, $R_{13}$, $R_{14}$ and $R_{15}$ in Formula (1) each independently represent an alkyl group or an acylamino group.

Since more excellent light fastness and moisture resistance are obtained, it is preferable that groups having an electron donating property are present at the ortho positions of the B rings. Therefore, it is preferable that $R_1$, $R_5$, $R_{11}$ and $R_{15}$ in Formula (1) each independently represent an alkyl group. Although depending on the structures of other portions, when groups having electron donating property are present at the ortho positions of the B rings, the color developability is improved in some cases.

Since more excellent light fastness and moisture resistance are obtained, it is preferable that groups having an electron donating property are present at the meta positions of the B rings. Therefore, it is preferable that at least one of $R_2$ and $R_4$ in Formula (1) and at least one of $R_{12}$ and $R_{14}$ each independently represent an acylamino group.

Since more excellent ozone resistance and light fastness are obtained, it is preferable to select a hydrogen atom or a group having an electron withdrawing property as the group directly bonded to the C ring. Therefore, it is preferable that $R_{21}$, $R_{22}$, $R_{23}$ and $R_{24}$ in Formula (1) each independently represent a hydrogen atom, a halogen atom, an acyl group, a nitro group, a cyano group, a sulfonic acid group or a carboxylic acid group. In particular, since more excellent ozone resistance and light fastness are obtained, it is preferable to select a hydrogen atom or a group having high electron withdrawing property as the group directly bonded to the C ring. Therefore, it is preferable that $R_{21}$, $R_{22}$, $R_{23}$ and $R_{24}$ in Formula (1) each independently represent a hydrogen atom or a sulfonic acid group.

Since more excellent light fastness is obtained, it is preferable to select a group having low electron withdrawing property as the group bonded to the nitrogen atom. Therefore, it is preferable that at least one of $R_{10}$ and $R_{20}$ in Formula (1) is preferably a hydrogen atom, an alkyl group, an aryl group or an aralkyl group. In particular, since particularly excellent light fastness is obtained, it is more preferable that at least one of $R_{10}$ and $R_{20}$ in Formula (1) is a hydrogen atom and it is particularly preferable that both $R_{10}$ and $R_{20}$ are hydrogen atoms.

Since synthesis and purification can be performed by a small number of processes and the yield and the purity of a synthesized compound (mixture) is easily increased, it is preferable for the compound represented by Formula (1) to have a symmetrical structure. Therefore, it is preferable that $R_1$ and $R_{11}$, $R_2$ and $R_{12}$, $R_3$ and $R_{13}$, $R_4$ and $R_{14}$, $R_5$ and $R_{15}$, $R_6$ and $R_{16}$, $R_7$ and $R_{17}$, $R_8$ and $R_{18}$, and $R_9$ and $R_{19}$ in Formula (1) each independently represent the same group.

The compound represented by Formula (1) has tautomers. Examples of the tautomers include compounds represented by the following formulae (1a), (1b) and (1c) and the like in addition to the compound represented by Formula (1). In an example embodiment, the compound represented by Formula (1) includes these compounds (tautomers) and their salts. $R_1$ to $R_{24}$ in Formulae (1a), (1b) and (1c) are defined the same as $R_1$ to $R_{24}$ in Formula (1)

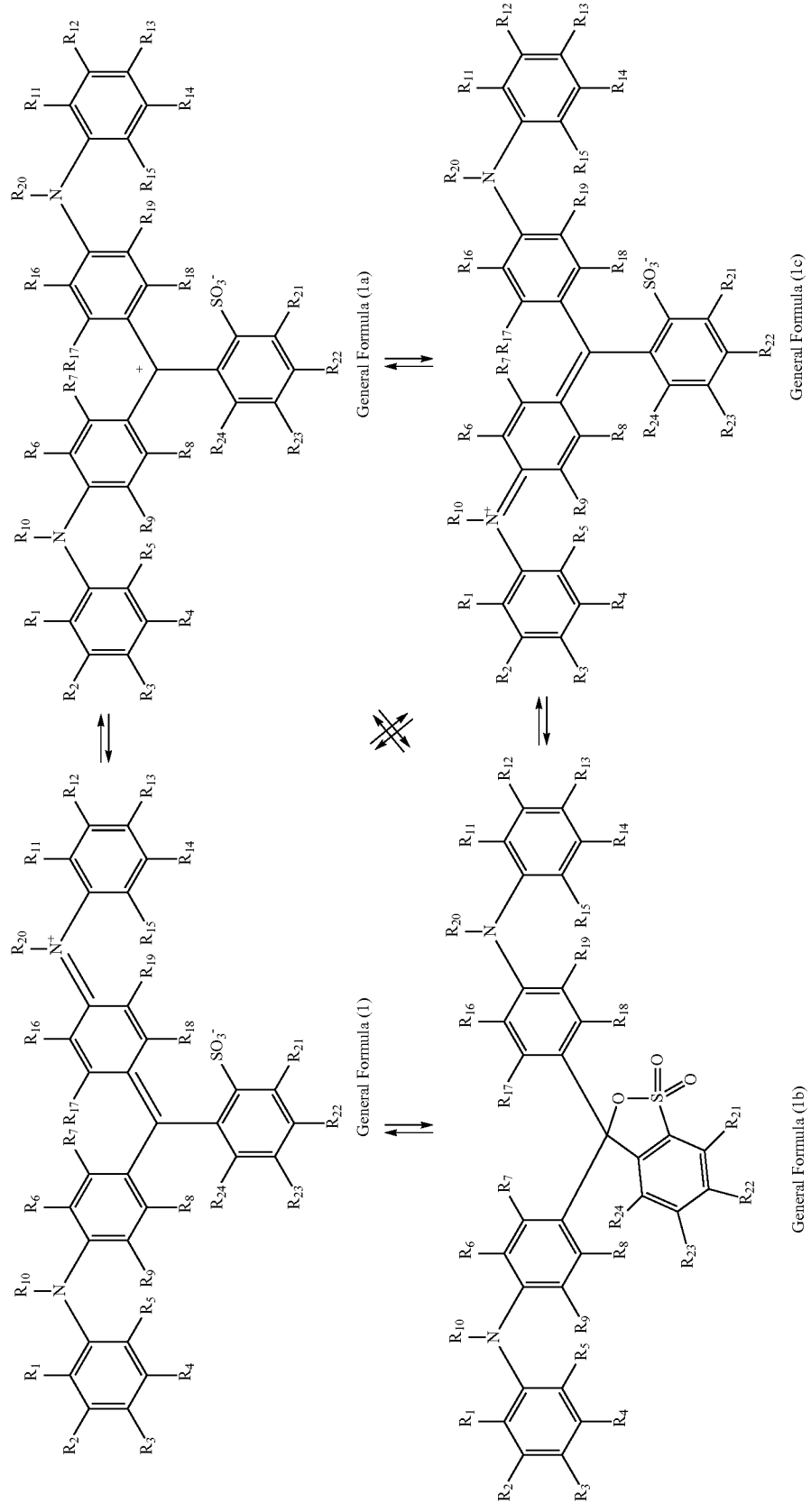

The compound represented by Formula (1) can be synthesized based on known methods. An example of a synthetic scheme is shown below. $R_1$ to $R_{24}$ in compounds (A) to (J) in the synthetic schemes are synonymous with $R_1$ to $R_{24}$ in Formula (1). The compound represented by Formula (1) can be synthesized as a mixture of a plurality of isomers different in the type, the number and the position of substituents but, for convenience, the compound represented by Formula (1) is referred to as "compound" also including the case where the compound represented by Formula (1) is a mixture. Although the compound to be used in each synthetic scheme is a free acid type, salt type compounds may be used.

Liquid medium to be used in the condensation process and the oxidation process of the synthetic scheme 1 is described. The condensation process and the oxidation process can be performed in the absence of solvent but it is preferable to use liquid medium. In the condensation process and the oxidation process, water, methanol, ethanol, n-propanol, isopropanol, n-butanol, tert-butanol, ethylene glycol, glycerol, tetrahydrofuran, N,N-dimethyl formamide, N,N-dimethyl acetamide, N-methyl-2-pyrrolidone, 1,3-dimethyl-2-imidazolidinone, dimethylsulfoxide, sulfolane, N,N'-dimethylpropyleneurea, chlorobenzene, 1,2-dichlorobenzene, nitromethane, nitrobenzene, and the like are preferably used alone or as a mixture, for example. The liquid medium to be

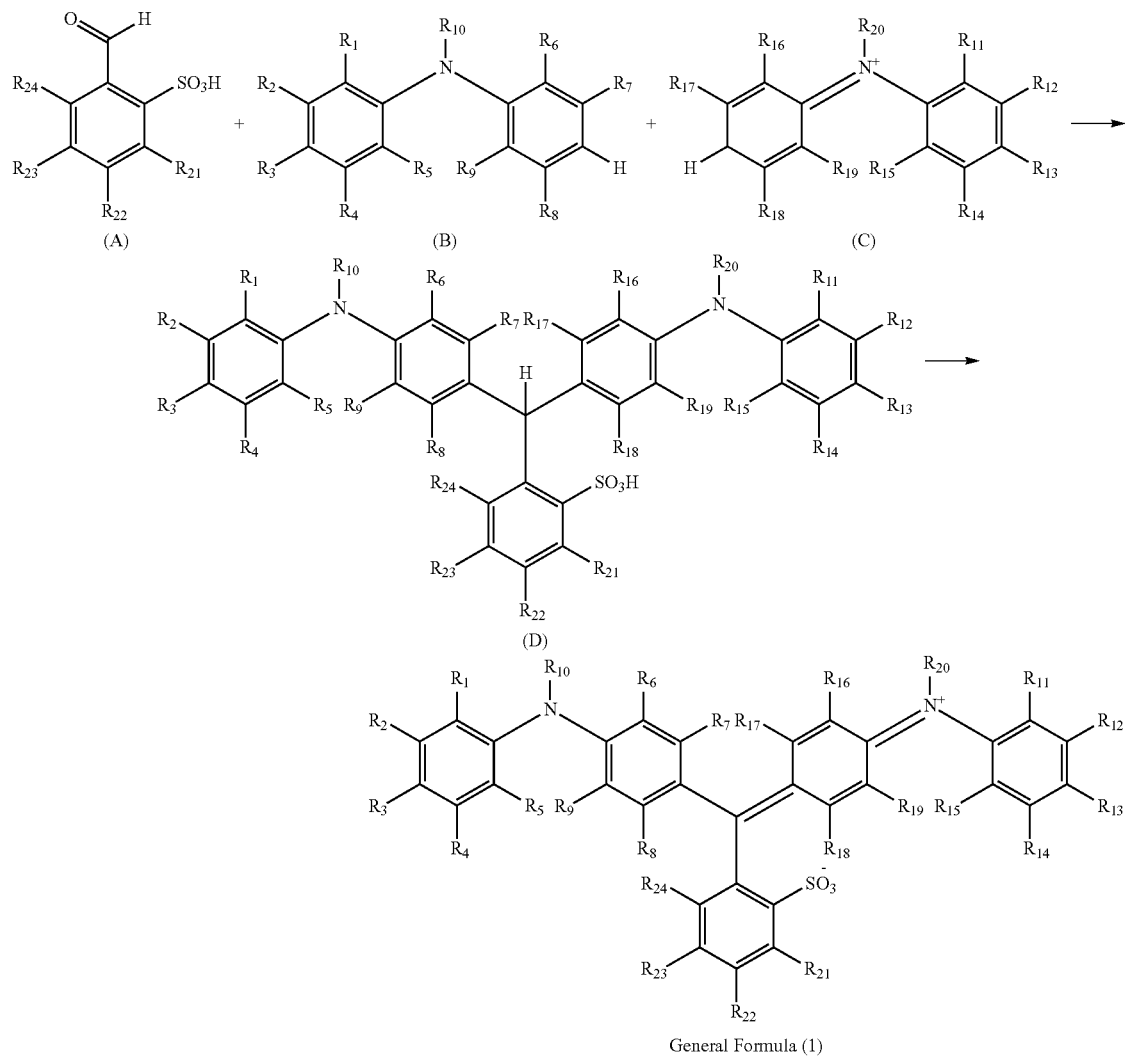

In the synthetic scheme 1 shown above as an example, the compound represented by Formula (1) can be obtained through a condensation process of condensing the compounds (A), (B) and (C) to obtain the compound (D) and an oxidation process of oxidizing the compound (D). The condensation process and the oxidation process can be performed in the presence of a liquid medium, a condensing agent, an oxidizing agent, and the like, as necessary.

used in the condensation process and the oxidation process may be the same or different.

A condensing agent to be used in the condensation process of the synthetic scheme 1 is described. Examples of the condensing agents include, for example, sulfuric acid, hydrochloric acid, phosphoric acid, acetic acid, formic acid, aluminum chloride, zinc chloride, p-toluenesulfonic acid, and the like. The reaction temperature in the condensation process is preferably 50° C. to 140° C. and more preferably 60° C. to 120° C.

conditions (specifically, pH of about 2 to 7). The reaction temperature in the oxidation process is preferably 10° C. to 80° C. and more preferably 20° C. to 50° C.

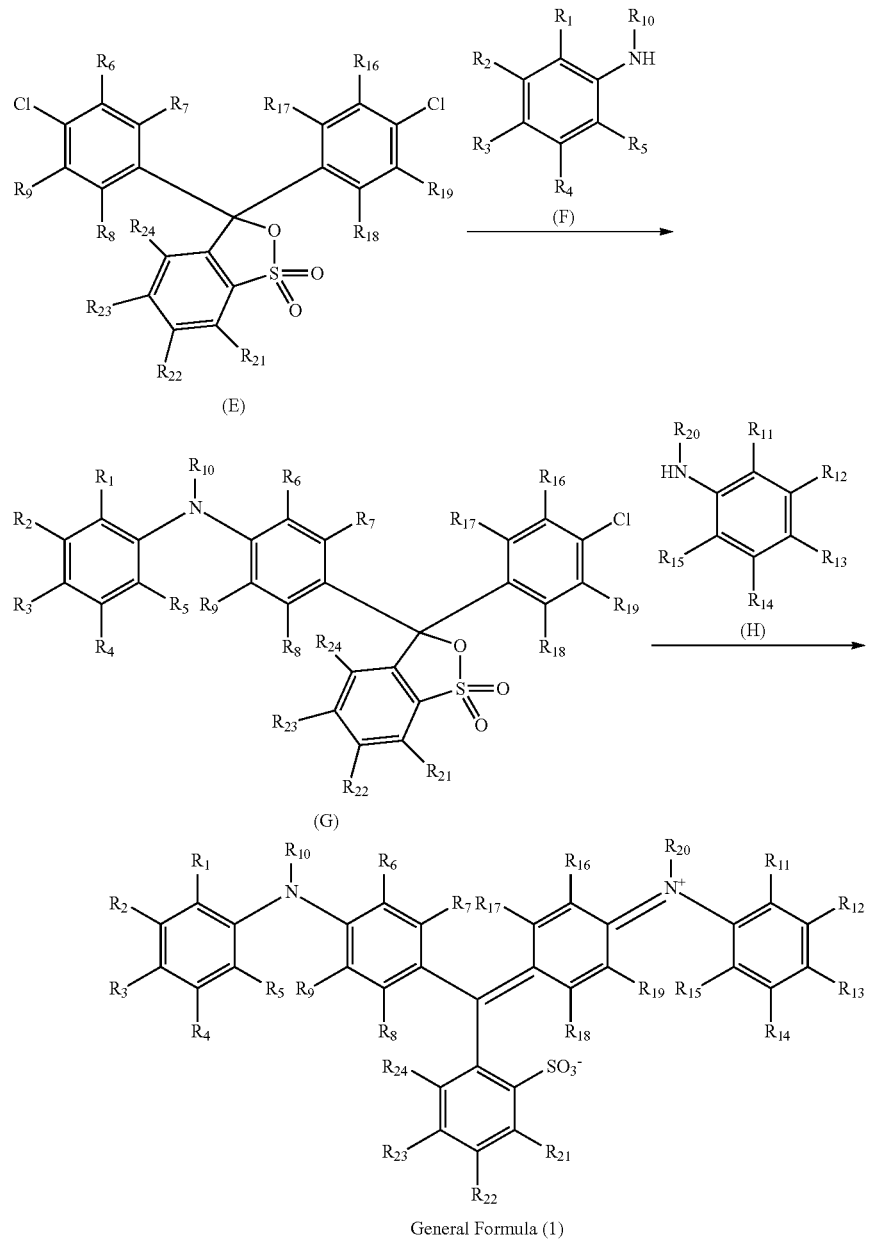

When a compound in which $R_1$ and $R_{11}$, $R_2$ and $R_{12}$, $R_3$ and $R_{13}$, $R_4$ and $R_{14}$, and $R_5$ and $R_{15}$ in Formula (1) each represent the same group is synthesized, the same type of compound can be used as the compounds (B) and (C) in the synthetic scheme 1.

An oxidizing agent to be used in the oxidation process of the synthetic scheme 1 is described. Examples of the oxidizing agents include, for example, lead oxide, zinc oxide, iron oxide, manganese oxide, hydrogen peroxide, chloranil, oxygen, and the like. The pH of the liquid medium in the oxidation process is preferably set to neutral to acidic The compound represented by Formula (1) can also be synthesized according to the synthetic scheme 2 shown above. In the synthetic scheme 2, the compound represented by Formula (1) can be obtained through a first condensation process of condensing the compounds (E) and (F) to obtain the compound (G) and a second condensation process of condensing the compounds (G) and (H). The first and second condensation processes can be performed in the presence of a liquid medium, a condensing agent, and the like, as necessary.

Liquid medium to be used in the first and second condensation processes of the synthetic scheme 2 is described.

The first and second condensation processes can be performed in the absence of a solvent but it is preferable to use liquid medium. In the first and second condensation processes, methanol, ethanol, n-propanol, isopropanol, n-butanol, tert-butanol, ethylene glycol, glycerol, tetrahydrofuran, N,N-dimethyl formamide, N,N-dimethyl acetamide, N-methyl-2-pyrrolidone, 1,3-dimethyl-2-imidazolidinone, dimethylsulfoxide, sulfolane, N,N'-dimethylpropyleneurea, chlorobenzene, 1,2-dichlorobenzene, nitromethane, nitrobenzene, and the like are preferably used alone or as a mixture, for example. The liquid medium to be used in the first and second condensation processes may be the same or different.

A condensing agent to be used in the first and second condensation processes of the synthetic scheme 2 is described. Examples of the condensing agents include, for example, sodium tert-butoxide, triethylamine, sodium hydroxide, magnesium oxide, zinc chloride, aluminum chloride, and the like. The condensing agents to be used in the first and second condensation processes may be the same or different. The reaction temperature in the first condensation process is preferably 60° C. to 100° C. and more preferably 70° C. to 90° C. The reaction temperature in the second condensation process is preferably 100° C. to 220° C. and more preferably 110° C. to 180° C.

When a compound in which $R_1$ and $R_{11}$, $R_2$ and $R_{12}$, $R_3$ and $R_{13}$, $R_4$ and $R_{14}$, and $R_5$ and $R_{15}$ in Formula (1) each represent the same group is synthesized, the same type of compound can be used as the compounds (F) and (H).

above. In the synthetic scheme 3, a compound (I) (equivalent to the case where $R_6$ of the compound represented by Formula (1) in the synthetic schemes 1 and 2 is a hydrogen atom) is synthesized according to the synthetic schemes 1 and 2 and the like. Thereafter, the compound represented by Formula (1) is obtained through a condensation process of condensing the compounds (I) and (J) The synthetic scheme 3 is shown taking the case where a compound represented by the $R_6$-LG structure is used as the compound (J) as an example, for convenience, and LG in the compound (J) means a desorption group. Examples of the compound (J) include, for example, N-chlorosuccinimide, acetyl chloride, chlorosulfuric-acid, fuming nitric acid, and the like.

Liquid medium to be used in the condensation process of the synthetic scheme 3 is described. The condensation process can be performed in the absence of a solvent but it is preferable to use liquid medium. In the condensation process, water, sulfuric acid, phosphoric acid, acetic acid, formic acid, methanol, ethanol, n-propanol, isopropanol, n-butanol, tert-butanol, ethylene glycol, glycerol, tetrahydrofuran, ethyl acetate, butyl acetate, N,N-dimethyl formamide, N,N-dimethyl acetamide, N-methyl-2-pyrrolidone, 1,3-dimethyl-2-imidazolidinone, dimethylsulfoxide, sulfolane, N,N'-dimethylpropyleneurea, dichloromethane, chloroform, carbon tetrachloride, acetonitrile, chlorobenzene, dichlorobenzene, nitromethane, nitrobenzene, and the like are preferably used alone or as a mixture, for example. The liquid medium to be used in the condensation process may

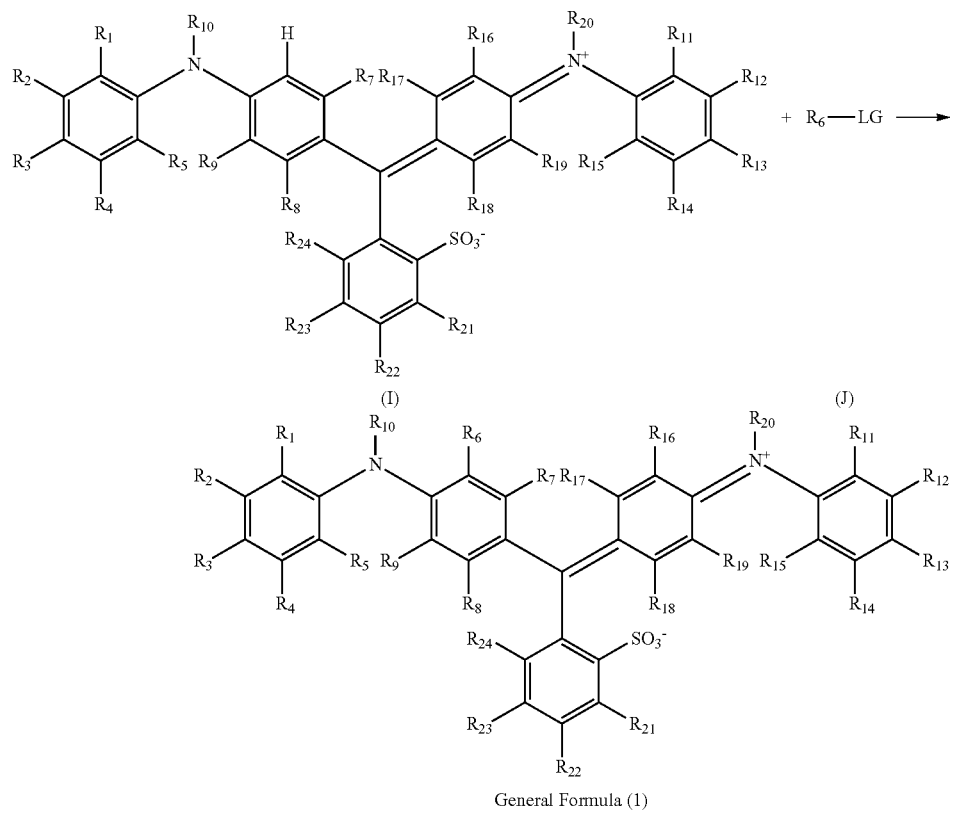

Synthetic scheme 3

General Formula (1)

The compound represented by Formula (1) can also be synthesized according to the synthetic scheme 3 shown be the same as or different from the liquid medium to be used in order to obtain the compound (I).

A condensing agent to be used in the condensation process of the synthetic scheme 3 is described. Examples of the condensing agents include sulfuric acid, hydrochloric acid, phosphoric acid, acetic acid, formic acid, aluminum chloride, zinc chloride, iron chloride, and the like, for example. The reaction temperature in the condensation process is preferably 0° C. to 60° C. and more preferably 10° C. to 50° C.

The compound which is the final product to be obtained by each synthetic scheme shown above is processed according to a post-processing method of a usual organic synthesis reaction, and then purified, whereby the compound can be utilized for desired use of coloring materials (dyes) of an ink, a toner, and the like, for example. For the identification of the compound represented by Formula (1), $^1$H-NMR analysis, LC/MS analysis, UV/Vis spectroscopic analysis, and the like are usable.

The compound represented by Formula (1) has high color developability and is excellent in ozone resistance, light fastness and moisture resistance. The compound represented by Formula (1) can be suitably used as coloring materials for various kinds of coloring compositions, such as print, paint, pens and pencils, ink jet, thermal transfer, sublimation type heat transfer and electrophotography. Moreover, the compound represented by Formula (1) can also be suitably used as coloring materials to be applied to optical recording, color filters, and the like in addition to the various kinds of coloring compositions.

Ink

An ink containing the compound represented by Formula (1) described above as a coloring material (dye) is suitably usable for ink jet. For example, the content (% by mass) of the compound represented by Formula (1) in the ink is preferably 0.10% by mass or more to 10.00% by mass or less and more preferably 0.20% by mass or more to 5.00% by mass or less based on the total ink mass.

Hereinafter, other components forming the ink of the present disclosure are described.

Other Coloring Materials

In the ink of the present disclosure, a compound having a different structure from that of the compound represented by the Formula (1) can be contained as a coloring material besides the compound represented by Formula (1). The present inventors have found that at least any one of the ozone resistance, the light fastness and the moisture resistance is further improved due to the ink of such a configuration without impairing the excellent color developability of the compound represented by Formula (1).

Examples of the compounds (other coloring materials) usable in addition to the compound represented by Formula (1) and having structures different from Formula (1) include pigments, dyes, and the like and dyes are more preferably used. As the other coloring materials, substances of any hue classified into cyan, magenta, yellow, red, blue, green, black, and the like may be used. In particular, dyes having a hue in a region from cyan to blue are preferably used and dyes having a cyan hue are more preferably used. Dyes, such as compounds having a triphenylmethane skeleton (compounds having a different structure from Formula (1)) and compounds having a phthalocyanine skeleton, are particularly preferably used. In particular, the compounds having a phthalocyanine skeleton are more preferably used. More specifically, it is preferable to use compounds having the maximum absorption wavelength ($\lambda_{max}$) in water in the range of 580 to 630 nm, particularly in the range of 590 to 620 nm, and more particularly in the range of 600 to 615 nm from the viewpoint of obtaining a further improvement effect of color developability.

Examples of central elements of the compounds having a phthalocyanine skeleton include a hydrogen atom, copper, aluminum, zinc, iron, nickel, gallium, and the like, and copper is preferable among the above. Moreover, at least one of four aromatic rings located in the outside of the phthalocyanine skeleton is preferably a heterocycle and more preferably a nitrogen containing aromatic ring, such as a pyridine ring or a pyrazine ring. By the use of the compounds having a phthalocyanine skeleton, the color developability, the ozone resistance and the light fastness can be increased with good balance.

Examples of the compounds having a triphenylmethane skeleton include, for example, C.I. Acid Blue: 1, 3, 5, 7, 9, 11, 13, 15, 17, 22, 24, 26, 34, 48, 75, 83, 84, 86, 88, 90, 91, 99, 100, 103, 104, 108, 109, 110 and 119, and the like.

Examples of the compounds having a phthalocyanine skeleton include C.I. Direct Blue: 6, 22, 25, 71, 78, 86, 87, 90, 106, 189, 199, 262, 264, 276, 282 and 314, C.I. Acid Blue: 9, 22, 40, 59, 93, 102, 104, 113, 117, 120, 167, 185, 197, 224, 228, 229, 234, 242, 243, 249, 254, 275, 279, 283, 310 and 357, and the like. Moreover, those described in Japanese Patent Laid-Open No. 2004-323605, International Publication No. WO2007/091631, International Publication No. WO2010/119676, Japanese Patent Laid-Open No. 2003-231834, and the like are mentioned. Specifically, the compound represented by the following formula (i), the compound represented by the following formula (ii), and the like are mentioned. It is a matter of course that the disclosure is not limited to the following compounds.

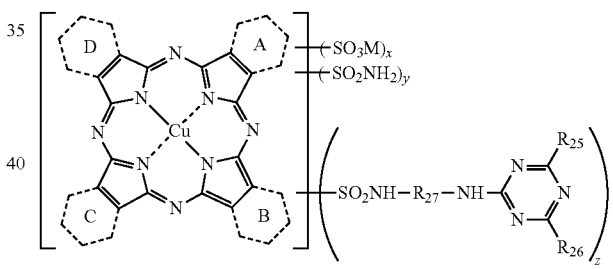

In Formula (i), the rings A, B, C and D represented by the dashed lines each independently represent an aromatic ring or a heteroaromatic ring. $R_{25}$ represents an anilino group substituted with 1 to 3 anionic groups. $R_{26}$ represents an amino group or an alkoxy group. $R_{27}$ represents an alkylene group. Ms each independently represent a hydrogen atom, alkali metal, ammonium or organic ammonium. X represents 0 to 4, y represents 1 to 3, z represents 1 to 3 and x+y+z represents 1 to 4.

As the anionic group, a carboxylic acid group, a sulfonic acid group, a phosphate group, a phosphonic acid group, and the like can be mentioned. These anionic groups may be either a free acid type or a salt type, for example. Examples of counterions forming salts include the same substances as those mentioned for the sulfonic acid group or the carboxylic acid group in Formula (1). The alkoxy group is preferably one having 1 to 4 carbon atoms. For example, a methoxy group, an ethoxy group, a propoxy group, a butoxy group, and the like are mentioned. The alkylene group is preferably one having 1 to 4 carbon atoms. For example, a methylene group, an ethylene group, a propylene group, a butylene group, and the like are mentioned.

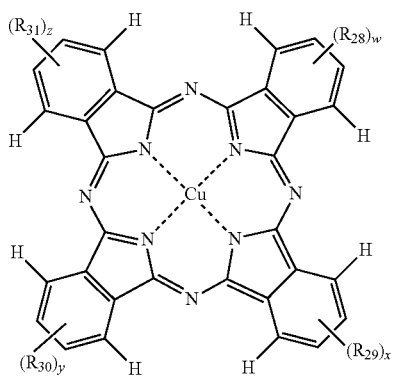

(ii)

In Formula (ii), $R_{28}$, $R_{29}$, $R_{30}$ and $R_{31}$ each independently represent —SO—Z, —SO$_2$—Z or —SO$_2$NR$_{32}$R$_{33}$. Zs each independently represent an alkyl group, an aralkyl group or an aryl group. $R_{32}$ and $R_{33}$ each independently represent a hydrogen atom, an alkyl group, an aralkyl group or an aryl group. w, x, y and z represent each independently represent 1 or 2.

It is preferable that Z, $R_{32}$ and $R_{33}$ each independently represent the following substance. The alkyl group is preferably one having 1 to 10 carbon atoms. For example, a methyl group, an ethyl group, a propyl group, a butyl group, and the like are mentioned. The aralkyl group is preferably one having 7 to 12 carbon atoms. For example, a benzyl group, a phenethyl group, and the like are mentioned. The aryl group is preferably one having 6 to 10 carbon atoms. For example, a phenyl group, a naphthyl group, and the like are mentioned. The alkyl group, the aralkyl group and the aryl group of Z, $R_{32}$ and $R_{33}$ may have substituents, such as an anionic group, such as a sulfonic acid group; and a hydroxy group. The hydrocarbon chain of an alkyl group and the like may be interposed by an atomic group, such as —SO$_2$NH—.

Specific examples of the compounds represented by Formula (i) and (ii) include phthalocyanine compounds 1 to 4 and the like having the following structures in the form of free acid.

Phthalocyanine compound 1

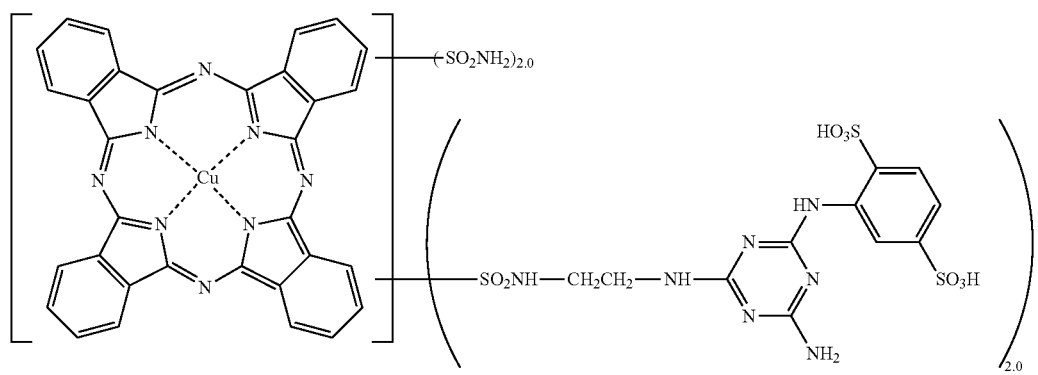

Phthalocyanine compound 2

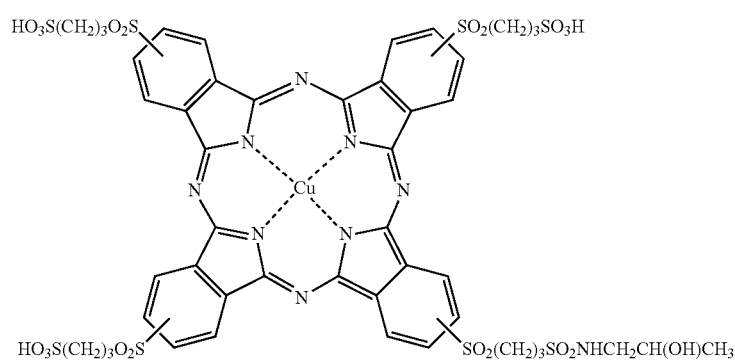

-continued

Phthalocyanine compound 3

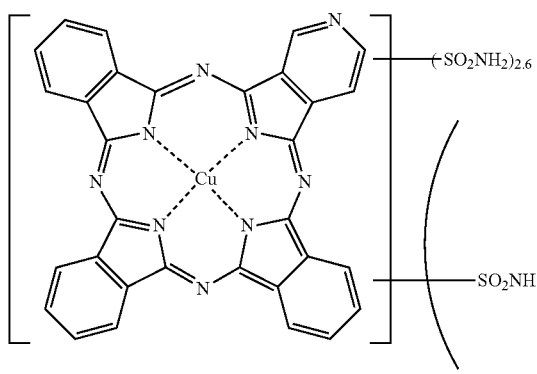 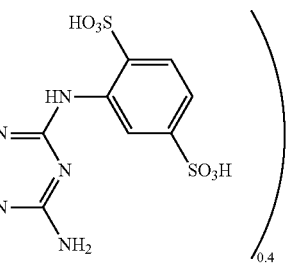

Phthalocyanine compound 4

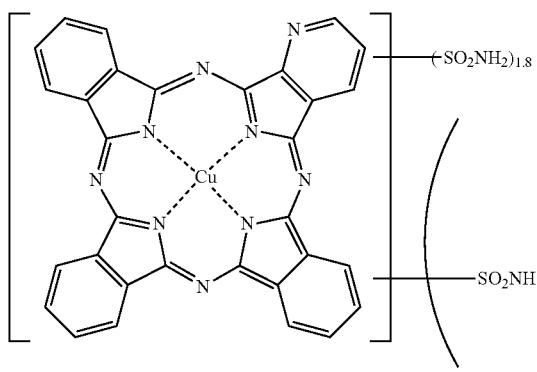 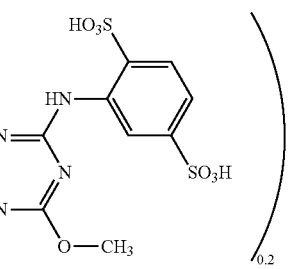

When the compound having a structure different from Formula (1) is used, the content (% by mass) of the compound in the ink is preferably 0.10% by mass or more to 10.00% by mass or less based on the total ink mass. Furthermore, the content is more preferably 0.30% by mass or more to 5.00% by mass or less. When the compound having a structure different from Formula (1) is used in addition to the compound represented by Formula (1) as coloring materials of the ink, the content of each compound is preferably set as follows. More specifically, the content (% by mass) of the compound represented by Formula (1) in the ink is preferably 0.20% by mass or more based on the total ink mass in order to obtain a higher level of color developability. The upper limit of the content (% by mass) of the compound represented by Formula (1) in the ink in this case is preferably 10.00% by mass or less and more preferably 5.00% by mass or less as in the case described above. The total content (% by mass) of each compound (coloring material) in the ink is preferably 0.10% by mass or more to 10.00% by mass or less based on the total ink mass.

As a result of an examination by the present inventors, a finding was obtained that, by compounding the compound represented by Formula (1) and the compound having a structure different from Formula (1) at a specific mass ratio in the ink, the ozone resistance and the light fastness can be further improved while maintaining the high level of color developability. Specifically, the content (% by mass) of the compound represented by Formula (1) is preferably 0.06 times or more to 6.00 times or less the content (% by mass) of the compound having a structure different from Formula (1) in terms of mass ratio based on the total ink mass. The mass ratio is more preferably 0.10 times or more to 2.00 times or less.

Liquid Medium

For the ink of the present disclosure, water, organic solvents or a mixture thereof can be used. The content (% by mass) of the liquid medium in the ink is preferably 50.0% by mass or more to 99.0% by mass or less based on the total ink mass.

In the case of an aqueous ink, it is preferable to use water or an aqueous medium which is a mixed solvent of water and a water-soluble organic solvent as the liquid medium. As the water, deionized water (ion exchanged water) is preferably used. The content (% by mass) of the water in the ink is preferably 10.0% by mass or more to 90.0% by mass or less based on the total ink mass. The content (% by mass) of the water-soluble organic solvent in the ink is preferably 5.0% by mass or more to 90.0% by mass or less and more preferably 10.0% by mass or more to 50.0% by mass or less based on the total ink mass. When used as an aqueous ink for ink jet, the ejection stability from a recording head can be sufficiently satisfied when the content of the water or the water-soluble organic solvent is within the ranges mentioned above.

The water-soluble organic solvent usable in the case of an aqueous ink is not particularly limited insofar as it is soluble in water (preferably one dissolved in water at an arbitrary ratio at 25° C.). Specifically, monohydric or polyhydric alcohols, alkylene glycols, glycol ethers, nitrogen containing polar compounds and sulfur containing polar compounds can be used.

In the case of an oil-based ink, an organic solvent can be used as the liquid medium. The content (% by mass) of the organic solvent in the ink is preferably 50.0% by mass or more to 99.0% by mass or less and more preferably 70.0% by mass or more to 95.0% by mass or less based on the total ink mass. When used as an oil-based ink for ink jet, the ejection stability from a recording head can be sufficiently satisfied when the content of the organic solvent is within the ranges mentioned above.

Examples of organic solvents usable in the case of an oil-based ink include those not having water solubility in addition to the water-soluble organic solvents mentioned above. Specifically, hydrocarbon compounds, ketones, ethers, acetate esters, aromatic compounds, and the like can be used.

Other Additives

The ink of the present disclosure may contain organic compounds which are solid at a normal temperature, such as polyhydric alcohols, such as trimethylolpropane and trimethylolethane, urea, urea derivatives, such as ethyleneurea, besides the components described above, as necessary. The ink may further contain various additives, such as a surfactant, a pH adjuster, a preservative, an antifungal agent, an antioxidant, a reduction inhibitor, an evaporation promoter, a chelating agent and resin, as necessary.

Ink Cartridge

An ink cartridge according to an embodiment of the present disclosure includes an ink and an ink storage portion. The ink stored in the ink storage portion is the foregoing ink according to an embodiment of the present disclosure.

Ink Jet Recording Method

An ink jet recording method according to an embodiment of the present disclosure is a method in which the foregoing ink according to an embodiment of the present disclosure is ejected from a recording head of an ink jet system to record an image on a recording medium. Examples of a method for ejecting an ink include a method in which mechanical energy is applied to an ink; and a method in which thermal energy is applied to an ink. In an embodiment of the present disclosure, a method in which thermal energy is applied to an ink may be employed. The ink jet recording method may include known steps, except that the ink according to an embodiment of the present disclosure is used.

EXAMPLES

Hereinafter, the disclosure is described in more detail with reference to Examples and Comparative Examples but the disclosure is not limited to the following Examples. "Part(s)" and "%" for the component amount are on a mass basis unless otherwise particularly specified.

Identification of Compounds Represented by Formula (1)

Compounds represented by Formula (1) synthesized below were identified by each of the following analysis methods.

[1] $^1$H-NMR spectroscopic analysis: $^1$H nuclear magnetic resonance spectroscopic analysis (ECA-400; manufactured by JEOL)

[2] LC/MS analysis: LC/TOF MS (LC/MSD TOF; manufactured by Agilent Technologies) As an ionizing method, an electrospray ionization method (ESI) was used.

Synthesis of Compounds Represented by Formula (1)

Exemplified Compound 9

3-aminobenzoic acid sodium salt (2.58 g) and the compound (E) in the above synthetic scheme 2 (1.84 g) were heated at a temperature of 110° C. for 6 hours in the presence of sodium tert-butoxide (3.16 g) in N,N-dimethyl formamide (20 mL) for reaction to give a reaction liquid. The obtained reaction liquid was cooled to room temperature, and then the filtrate obtained by filtration was concentrated under reduced pressure. To a component obtained by the concentration under reduced pressure, methanol (20 mL) was added and stirred. Thereafter, the resultant mixture was developed to acetone (200 mL), and then the precipitated solid was fractionated. After methanol was added to the obtained solid again, and then stirred, the cycle of developing the resultant mixture to acetone, and then fractionating the precipitated solid was repeated for purifying to give Exemplified Compound 9 (1.82 g) represented by the following structural formula.

Exemplified Compound 9

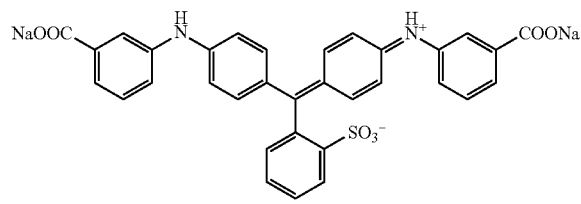

It was confirmed that the obtained Exemplified Compound 9 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 12.5 minutes: Purity=96.2% by area, m/z=591.1210 (M-2Na+H)$^-$

Exemplified Compound 11

2,6-dichlorodiphenylamine (4.86 g) and 4-formylbenzene-1,3-disodium disulfonate (3.17 g) were heated at a temperature of 60° C. for 50 hours in the presence of sulfuric acid (10.00 g) in water (20 mL) for reaction to give a reaction liquid. The obtained reaction liquid was cooled to room temperature, the reaction liquid was discharged onto ice (100 g), and then chloroform was added for liquid separation to extract the aqueous phase. To the obtained aqueous phase, manganese oxide (2.90 g) was added, and then the mixture was stirred at a temperature of 20 to 25° C. for 24 hours for reaction to give a reaction liquid. To the filtrate obtained by filtering the obtained reaction liquid, 2 mol/L of sodium hydroxide aqueous solution was added to adjust the pH of the liquid to 7.0. Thereafter, sodium chloride was added for salting-out, and then the precipitated solid was fractionated by filtration. The obtained solid was added into methanol (100 mL), the filtrate obtained by filtration was concentrated under reduced pressure, and then the resultant mixture was purified by column chromatography to thereby give Exemplified Compound 11 (0.93 g) represented by the following structural formula.

Exemplified Compound 11

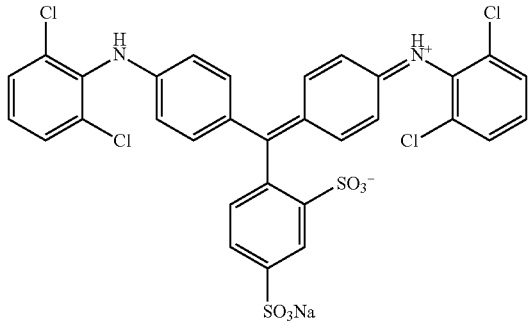

It was confirmed that the obtained Exemplified Compound 11 had the above-described structure by [2] LC/TOFMS analysis. The analysis results are shown below.

[2] LC/TOF MS Analysis (Eluate: 0.1% Acetic Acid Aqueous Solution-Methanol, ESI) Results:

Retention time 14.2 minutes: Purity=98.1% by area, m/z=718.9463 (M-Na)⁻

Exemplified Compound 14

4-(ethyl(phenyl)amino)sodium benzenesulfonate (2.16 g) and 2-sulfobenzaldehyde sodium salt (0.70 g) were heated at a temperature of 100° C. for 8 hours in the presence of sulfuric acid (0.54 g) in water (10 mL) for reaction to give a reaction liquid. The obtained reaction liquid was cooled to room temperature, manganese oxide (0.63 g) was added, and then the mixture was stirred at a temperature of 20 to 25° C. for 2 hours for reaction to give a reaction liquid. To the filtrate obtained by filtering the obtained reaction liquid, 2 mol/L of sodium hydroxide aqueous solution was added to adjust the pH of the liquid to 7.0. The liquid was concentrated under reduced pressure to give a solid. The obtained solid was added into methanol (50 mL), the filtrate obtained by filtration was concentrated under reduced pressure, and then the resultant mixture was purified by column chromatography to thereby give Exemplified Compound 14 (1.24 g) represented by the following structural formula.

Exemplified Compound 14

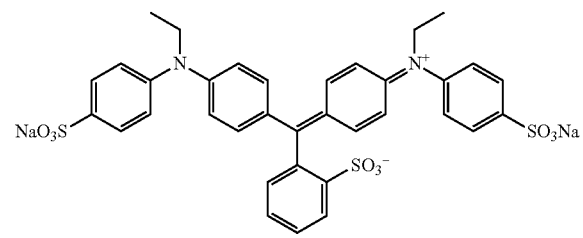

It was confirmed that the obtained Exemplified Compound 14 had the above-described structure by [1] ¹H-NMR analysis and [2] LC/TOF MS analysis. The analysis results are shown below.

[1] $^1$H-NMR (400 MHz, DMSO-d$_6$, Temperature of 80° C.) Results (FIG. 1):

δ (ppm)=7.90 (1H, d, J=7.8 Hz), 7.74 (4H, d, J=8.2 Hz), 7.55 (1H, t, J=7.6 Hz), 7.44 (1H, t, J=7.6 Hz), 7.32 (4H, d, J=8.4 Hz), 7.29 (4H, d, J=9.6 Hz), 6.96 (1H, d, J=7.3 Hz), 6.82 (4H, d, J=9.6 Hz), 3.95 (4H, q, J=7.1 Hz), 1.20 (6H, t, J=7.0 Hz)

[2] LC/TOF MS Analysis (Eluate: 0.1% Acetic Acid Aqueous Solution-Methanol, ESI) Results:

Retention time 10.8 minutes: Purity=98.9% by area, m/z=719.1253 (M-2Na+H)⁻

Exemplified Compound 17

2,4-dimethylaniline-6-sulfonic acid (8.43 g) and the compound (E) in the above synthetic scheme 2 (3.91 g) were heated at a temperature of 90° C. for 20 hours in the presence of sodium tert-butoxide (2.11 g) in 1,3-dimethyl-2-imidazolidinone (30 mL) for reaction to give a reaction liquid. The obtained reaction liquid was cooled to room temperature, and then filtered to fractionate the filtrate. The obtained filtrate was developed to acetone (500 mL), and then the precipitated solid was fractionated by filtration. After methanol was added to the obtained solid, and then stirred, the cycle of developing the resultant mixture to acetone, and then fractionating the precipitated solid was repeated for purifying to give Exemplified Compound 17 (4.74 g) represented by the following structural formula.

Exemplified Compound 17

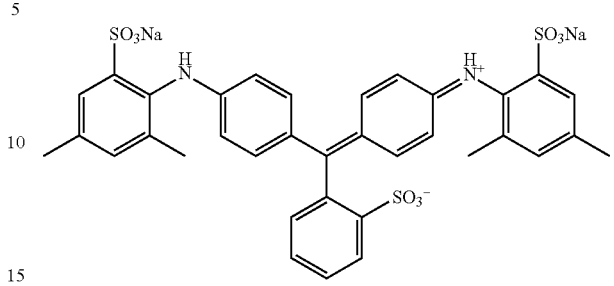

It was confirmed that the obtained Exemplified Compound 17 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 11.1 minutes: Purity=95.7% by area, m/z=719.1215 (M-2Na+H)⁻

Exemplified Compound 16

Exemplified Compound 17 (3.00 g) was added into fuming sulfuric acid (20.00 g) under ice cooling, and stirred at a temperature of 20 to 25° C. for 2 hours for reaction to give a reaction liquid. The obtained reaction liquid was discharged onto ice (100 g), and then the precipitated solid was fractionated by filtration. The obtained solid was washed with cold water, and then added into methanol (100 mL). Then, 2 mol/L of sodium hydroxide aqueous solution was added to adjust the pH of the liquid to 7.0. The filtrate obtained by filtering the liquid was concentrated under reduced pressure, and then the resultant mixture was purified by column chromatography to thereby give Exemplified Compound 16 (1.96 g) represented by the following structural formula.

Exemplified Compound 16

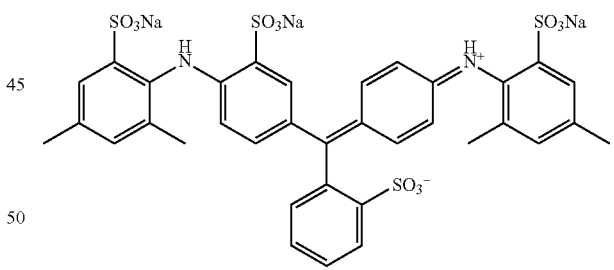

It was confirmed that the obtained Exemplified Compound 16 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 9.9 minutes: Purity=98.2% by area, m/z=799.0793 (M-3Na+2H)⁻

Exemplified Compound 18

4,4'-dimethyltriphenylmethane (5.57 g) and 4-formylbenzene-1,3-disodium disulfonate (3.17 g) were heated at a temperature of 80° C. for 24 hours in the presence of sulfuric acid (2.00 g) in dimethylsulfoxide (30 mL) for reaction to give a reaction liquid. The obtained reaction liquid was cooled to room temperature, the reaction liquid was discharged onto ice (100 g), and then chloroform was added for liquid separation to extract the aqueous phase. To the obtained aqueous phase, manganese oxide (2.90 g) was added, and then the mixture was stirred at a temperature of 20 to 25° C. for 24 hours for reaction to give a reaction liquid. To the filtrate obtained by filtering the obtained reaction liquid, 2 mol/L of sodium hydroxide aqueous solution was added to adjust the pH of the liquid to 7.0. Thereafter, water and sodium chloride were added for salting-out, and then the precipitated solid was fractionated by filtration. The obtained solid was added into methanol (100 mL), the filtrate obtained by filtration was concentrated under reduced pressure, and then the resultant mixture was purified by column chromatography to thereby give Exemplified Compound 18 (3.52 g) represented by the following structural formula.

Exemplified Compound 18

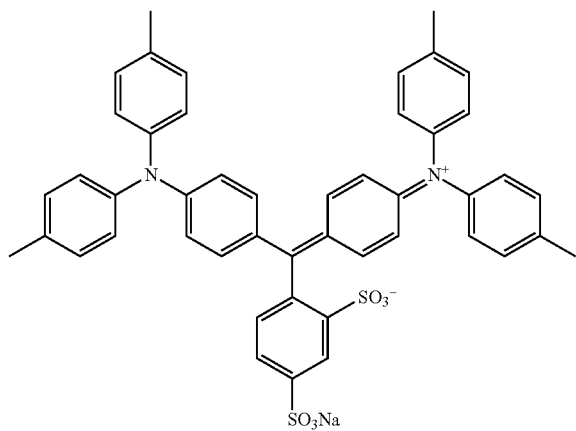

It was confirmed that the obtained Exemplified Compound 18 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 16.0 minutes: Purity=98.3% by area, m/z=791.2281 (M-Na)$^-$

Exemplified Compound 34

2-(mesitylamino)sodium benzoate (3.00 g) and 2-sulfobenzaldehyde sodium salt (1.19 g) were heated at a temperature of 60° C. for 50 hours in the presence of sulfuric acid (10.00 g) in water (20 mL) for reaction to give a reaction liquid. The obtained reaction liquid was cooled to room temperature, and then discharged onto ice (100 g). Then, the precipitated solid was fractionated by filtration. The obtained solid was washed with water several times. To the obtained solid, methanol (100 mL) was added, and then stirred at a temperature of 20 to 25° C. for 24 hours in the presence of manganese oxide (1.64 g) and phosphoric acid (0.50 g) for reaction to give a reaction liquid. To the filtrate obtained by filtering the obtained reaction liquid, 2 mol/L of sodium hydroxide aqueous solution was added to adjust the pH of the liquid to 7.0. The obtained liquid was concentrated under reduced pressure, and then the resultant mixture was purified by column chromatography to thereby give Exemplified Compound 34 (0.45 g) represented by the following structural formula.

Exemplified Compound 34

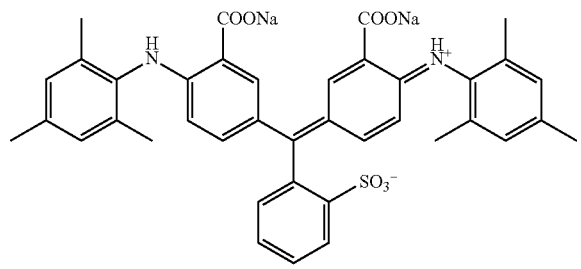

It was confirmed that the obtained Exemplified Compound 34 had the above-described structure by [1] $^1$H-NMR analysis and [2] LC/TOF MS analysis. The analysis results are shown below.

Figure 2:
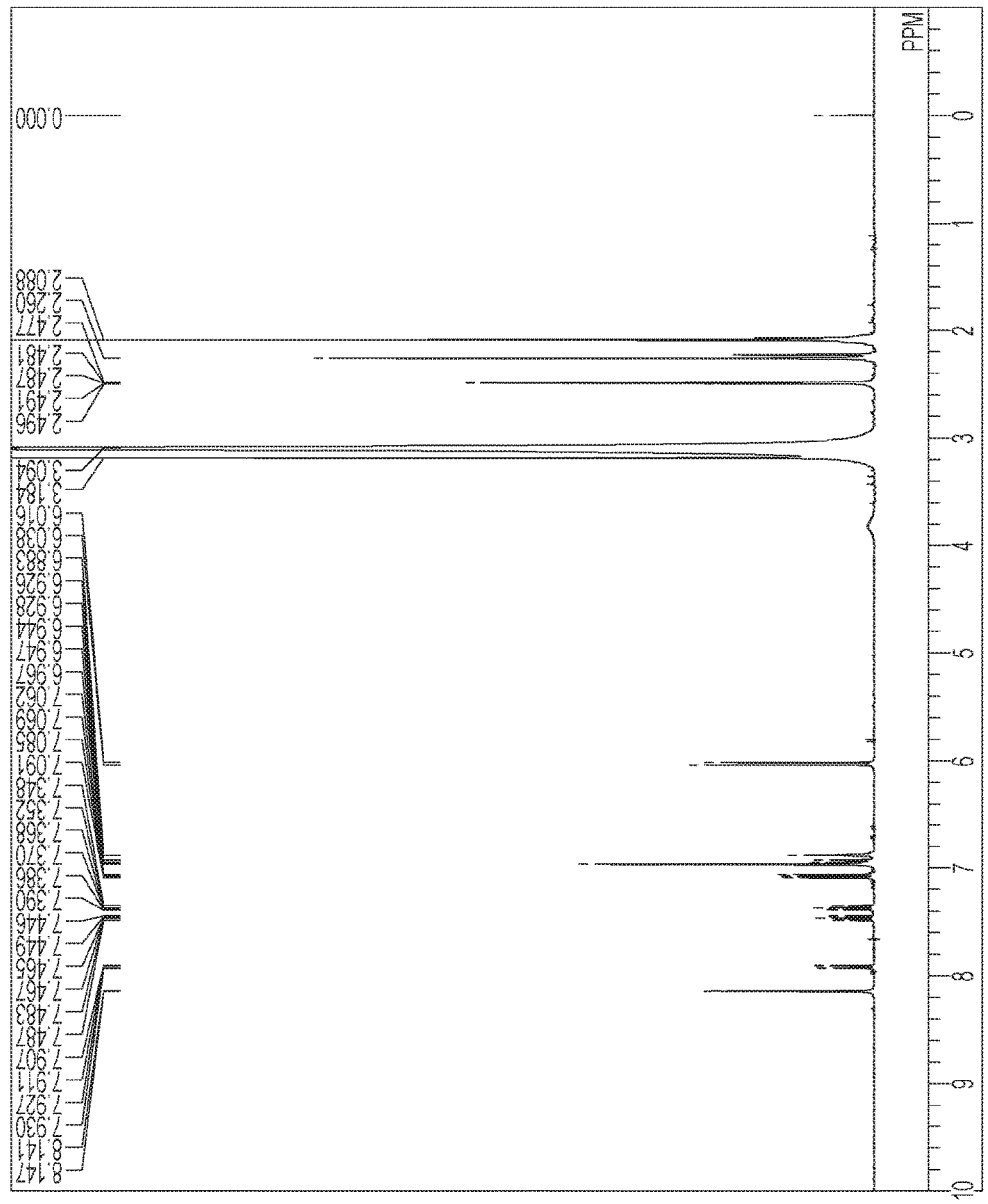
FIG. 2 is a chart showing the $^1$H-NMR analysis results of Exemplified Compound 34.

[1] $^1$H-NMR (400 MHz, DMSO-d$_6$, Temperature of 80° C.) Results (FIG. 2):

δ (ppm)=8.14 (2H, d, J=2.3 Hz), 7.92 (1H, dd, J=7.8, 1.4 Hz), 7.47 (1H, td, J=7.6, 1.2 Hz), 7.37 (1H, td, J=7.6, 1.2 Hz), 7.08 (2H, dd, J=8.9, 2.5 Hz), 6.97 (4H, s), 6.94 (1H, dd, J=7.6, 1.2 Hz), 6.88 (2H, d, J=3.2 Hz), 6.03 (2H, d, J=8.7 Hz), 2.26 (6H, s), 2.09 (12H, s)

[2] LC/TOF MS Analysis (Eluate: 0.1% Acetic Acid Aqueous Solution-Methanol, ESI) Results:

Retention time 13.3 minutes: Purity=95.7% by area, m/z=675.2207 (M-2Na+H)$^-$

Exemplified Compound 40

N-ethyl-2,4,6-trimethyl-N-phenylaniline (4.88 g) and 2-sulfobenzaldehyde sodium (2.13 g) were heated at a temperature of 100° C. for 30 hours in the presence of acetic acid (20.00 g) and sulfuric acid (2.00 g) in water (20 mL) for reaction to give a reaction liquid. The obtained reaction liquid was cooled to room temperature, manganese oxide (2.93 g) was added, and then the mixture was stirred at a temperature of 20 to 25° C. for 24 hours for reaction to give a reaction liquid. To the filtrate obtained by filtering the obtained reaction liquid, 2 mol/L of sodium hydroxide aqueous solution was added to adjust the pH of the liquid to 7.0. Heptane was added to the liquid for liquid separation to extract the aqueous phase. The obtained aqueous phase was concentrated under reduced pressure to give a solid. The obtained solid was added into methanol (100 mL), and then the filtrate obtained by filtration was concentrated under reduced pressure to give a solid. 3.00 g of the obtained solid was fractionated, added into fuming sulfuric acid (30.00 g) under ice cooling, and then stirred at a temperature of 20 to 25° C. for 3 days for reaction to give a reaction liquid. The obtained reaction liquid was discharged onto ice (100 g), and then the precipitated solid was fractionated by filtration. The obtained solid was washed with cold water, and then added into methanol (100 mL). Then, 2 mol/L of sodium hydroxide aqueous solution was added to adjust the pH of the liquid to 7.0. The filtrate obtained by filtering the liquid was concentrated under reduced pressure, and then the resultant mixture was purified by column chromatography to thereby give Exemplified Compound 40 (1.85 g) represented by the following structural formula.

Exemplified Compound 40

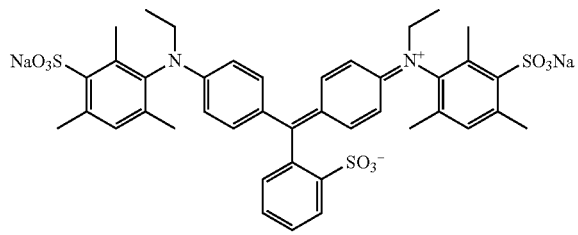

It was confirmed that the obtained Exemplified Compound 40 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 13.1 minutes: Purity=96.6% by area, m/z=803.2172 (M-2Na+H)⁻

Exemplified Compound 46

5-oxo-5-(2,4,6-trimethyl-3-(phenylamino)phenylamino) pentanoic acid (6.95 g) and 4-formylbenzene-1,3-disodium disulfonate (3.18 g) were heated at a temperature of 70° C. for 30 hours in the presence of sulfuric acid (2.00 g) in water (30 mL) for reaction to give a reaction liquid. The obtained reaction liquid was cooled to room temperature, and then discharged onto ice (100 g). Then, the precipitated solid was fractionated by filtration. The obtained solid was washed with water several times. To the obtained solid, methanol (100 mL) was added, and then stirred at a temperature of 20 to 25° C. for 24 hours in the presence of manganese oxide (2.90 g) and hydrochloric acid (0.50 g) for reaction to give a reaction liquid. To the filtrate obtained by filtering the obtained reaction liquid, 2 mol/L of sodium hydroxide aqueous solution was added to adjust the pH of the liquid to 7.0. The obtained liquid was concentrated under reduced pressure, and then the resultant mixture was purified by column chromatography to thereby give Exemplified Compound 46 (3.20 g) represented by the following structural formula.

Exemplified Compound 46

It was confirmed that the obtained Exemplified Compound 46 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 11.9 minutes: Purity=98.1% by area, m/z=925.2832 (M-3Na+2H)⁻

Exemplified Compound 47

N-(2,4,6-trimethyl-3-(phenylamino)phenyl)isobutylamide (6.05 g) and 4-formylbenzene-1,3-disodium disulfonate (3.17 g) were heated at a temperature of 70° C. for 30 hours in the presence of sulfuric acid (2.00 g) in dimethylsulfoxide (20 mL) for reaction to give a reaction liquid. The obtained reaction liquid was cooled to room temperature, manganese oxide (2.90 g) was added, and then the mixture was stirred at a temperature of 20 to 25° C. for 24 hours for reaction to give a reaction liquid. To the filtrate obtained by filtering the obtained reaction liquid, 2 mol/L of sodium hydroxide aqueous solution was added to adjust the pH of the liquid to 7.0. Thereafter, water and sodium chloride were added for salting-out, and then the precipitated solid was fractionated by filtration. The obtained solid was added into methanol (100 mL), and then the filtrate obtained by filtration was concentrated under reduced pressure. 3.00 g of the obtained solid was fractionated, added into fuming sulfuric acid (20.00 g) under ice cooling, and then stirred at a temperature of 20 to 25° C. overnight for reaction to give a reaction liquid. The obtained reaction liquid was discharged onto ice (100 g), and then the precipitated solid was fractionated by filtration. The obtained solid was washed with cold water, and then added into methanol (100 mL). Then, 2 mol/L of sodium hydroxide aqueous solution was added to adjust the pH of the liquid to 7.0. The filtrate obtained by filtering the liquid was concentrated under reduced pressure, and then the resultant mixture was purified by column chromatography to thereby give Exemplified Compound 47 (1.77 g) represented by the following structural formula.

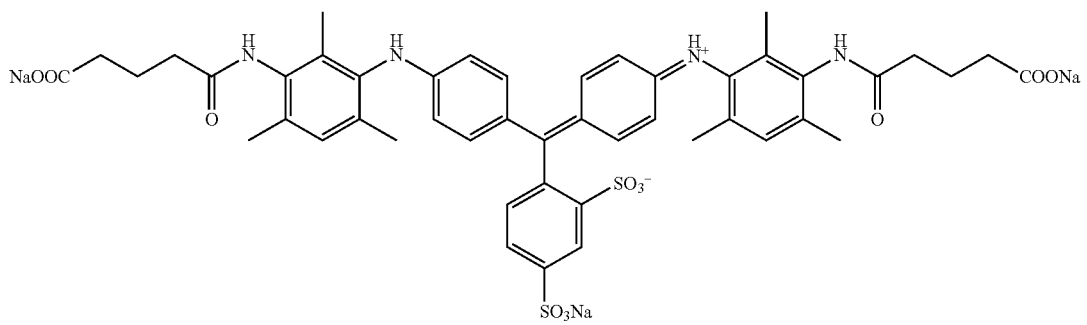

Exemplified Compound 47

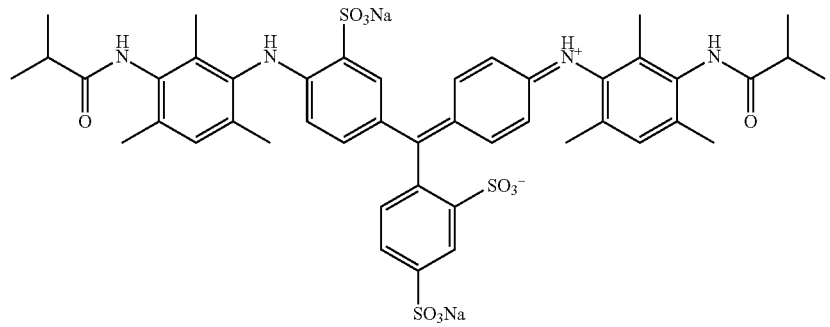

It was confirmed that the obtained Exemplified Compound 47 had the above-described structure by [2] LC/TOF MS analysis. The analysis results are shown below.

[2] LC/TOF MS Analysis (Eluate: 0.1% Acetic Acid Aqueous Solution-Methanol, ESI) Results:

Retention time 12.8 minutes: Purity=95.9% by area, m/z=917.2588 (M-2Na+H)⁻

Other Compounds

According to the synthetic methods of the compounds above, compounds having the structures shown in Tables 1 and 2 were synthesized as a free acid type (H type) The structures of these compounds were confirmed in the same manner as that of Exemplified Compounds above. In Tables 1 and 2, "Me" represents methyl, "Et" represents ethyl, "iPr" represents isopropyl, "Bu" represents n-butyl, "pTol" represents p-tolyl, and "Bz" represents benzyl.

TABLE 1

Exemplified Compounds of Formula (1)

| Exemplified Compounds | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|---|
| 1 | $SO_3H$ | H | OMe | H | H | H | H | H | H | H | H | H |
| 2 | $SO_3H$ | H | OMe | H | H | H | H | H | H | H | H | H |
| 3 | $SO_3H$ | H | OMe | H | H | H | H | H | H | H | $SO_3H$ | H |
| 4 | COOH | H | OMe | OMe | H | H | H | H | H | H | COOH | H |
| 5 | $SO_3H$ | H | H | H | H | H | H | H | H | H | $SO_3H$ | H |
| 6 | H | $SO_3H$ | H | H | H | H | H | H | H | H | H | $SO_3H$ |
| 7 | H | H | $SO_3H$ | H | H | H | H | H | H | H | H | H |
| 8 | COOH | H | H | H | H | H | H | H | H | H | COOH | H |
| 9 | H | COOH | H | H | H | H | H | H | H | H | H | COOH |
| 10 | H | H | COOH | H | H | H | H | H | H | H | H | H |
| 11 | Cl | H | H | H | Cl | H | H | H | H | H | Cl | H |
| 12 | Cl | H | H | H | Cl | H | H | H | H | Et | Cl | H |
| 13 | Cl | H | H | H | Cl | H | H | H | H | $C_3H_6COOH$ | Cl | H |
| 14 | H | H | $SO_3H$ | H | H | H | H | H | H | Et | H | H |
| 15 | H | H | $SO_3H$ | H | H | H | H | H | H | Et | H | H |
| 16 | $SO_3H$ | H | Me | H | Me | $SO_3H$ | H | H | H | H | $SO_3H$ | H |
| 17 | $SO_3H$ | H | Me | H | Me | H | H | H | H | H | $SO_3H$ | H |
| 18 | H | H | Me | H | H | H | H | H | H | pTol | H | H |
| 19 | H | H | Me | H | H | H | H | H | H | Bz | H | H |
| 20 | Me | $SO_3H$ | Me | H | Me | H | H | H | H | H | Me | H |
| 21 | Me | H | Me | H | Me | H | H | H | H | H | Me | H |
| 22 | Me | Me | Me | Me | Me | H | H | H | H | H | Me | Me |
| 23 | $SO_3H$ | H | Me | H | Me | $SO_3H$ | H | H | H | H | $SO_3H$ | H |
| 24 | $SO_3H$ | H | Me | H | Me | COOH | H | H | H | H | $SO_3H$ | H |
| 25 | $SO_3H$ | H | Me | H | Me | COOH | H | H | H | H | $SO_3H$ | H |
| 26 | Me | $SO_3H$ | Me | H | Me | $SO_3H$ | H | H | H | H | Me | $SO_3H$ |
| 27 | Me | $SO_3H$ | Me | H | Me | $SO_3H$ | H | H | H | H | Me | $SO_3H$ |

| Exemplified Compounds | $R_{13}$ | $R_{14}$ | $R_{15}$ | $R_{16}$ | $R_{17}$ | $R_{18}$ | $R_{19}$ | $R_{20}$ | $R_{21}$ | $R_{22}$ | $R_{23}$ | $R_{24}$ |
|---|---|---|---|---|---|---|---|---|---|---|---|---|
| 1 | OMe | H | H | H | H | H | H | H | H | H | H | H |
| 2 | OMe | H | H | H | H | H | H | H | H | $SO_3H$ | H | H |
| 3 | OMe | H | H | H | H | H | H | H | H | H | H | H |
| 4 | OMe | OMe | H | H | H | H | H | H | H | H | H | H |
| 5 | H | H | H | H | H | H | H | H | H | H | H | H |
| 6 | H | H | H | H | H | H | H | H | H | H | H | H |
| 7 | $SO_3H$ | H | H | H | H | H | H | H | H | H | H | H |
| 8 | H | H | H | H | H | H | H | H | H | H | H | H |
| 9 | H | H | H | H | H | H | H | H | H | H | H | H |
| 10 | COOH | H | H | H | H | H | H | H | H | H | H | H |
| 11 | H | H | Cl | H | H | H | H | H | H | $SO_3H$ | H | H |
| 12 | H | H | Cl | H | H | H | H | Et | H | $SO_3H$ | H | H |

TABLE 1-continued

Exemplified Compounds of Formula (1)

| | | | | | | | | | | | | |
|---|---|---|---|---|---|---|---|---|---|---|---|---|
| 13 | H | H | Cl | H | H | H | H | C$_3$H$_6$COOH | H | SO$_3$H | H | H |
| 14 | SO$_3$H | H | H | H | H | H | H | Et | H | H | H | H |
| 15 | SO$_3$H | H | H | H | H | H | H | Et | H | SO$_3$H | H | H |
| 16 | Me | H | Me | H | H | H | H | H | H | H | H | H |
| 17 | Me | H | Me | H | H | H | H | H | H | H | H | H |
| 18 | Me | H | H | H | H | H | H | pTol | H | SO$_3$H | H | H |
| 19 | Me | H | H | H | H | H | H | Bz | H | SO$_3$H | H | H |
| 20 | Me | H | Me | H | H | H | H | H | H | H | H | H |
| 21 | Me | H | Me | H | H | H | H | H | H | SO$_3$H | H | H |
| 22 | Me | Me | Me | H | H | H | H | H | H | SO$_3$H | H | H |
| 23 | Me | H | Me | SO$_3$H | H | H | H | H | H | H | H | H |
| 24 | Me | H | Me | COOH | H | H | H | H | H | H | H | H |
| 25 | Me | H | Me | COOH | H | H | H | H | H | SO$_3$H | H | H |
| 26 | Me | H | Me | H | H | H | H | H | H | H | H | H |
| 27 | Me | H | Me | H | H | H | H | H | H | SO$_3$H | H | H |

TABLE 2

Exemplified Compounds of Formula (1)

| Exemplified Compounds | R$_1$ | R$_2$ | R$_3$ | R$_4$ | R$_5$ | R$_6$ | R$_7$ | R$_8$ | R$_9$ | R$_{10}$ | R$_{11}$ | R$_{12}$ |
|---|---|---|---|---|---|---|---|---|---|---|---|---|
| 28 | Me | H | Me | H | Me | COMe | H | H | H | H | Me | H |
| 29 | Me | SO$_3$H | Me | H | Me | H | H | H | H | H | Me | SO$_3$H |
| 30 | Me | H | SO$_3$H | H | Me | Me | H | H | Me | H | Me | H |
| 31 | Me | SO$_3$H | Me | H | Me | NO$_2$ | H | H | H | H | Me | SO$_3$H |
| 32 | Me | SO$_3$H | Me | H | Me | Cl | H | H | H | H | Me | SO$_3$H |
| 33 | Me | H | Me | H | Me | Cl | H | H | H | H | Me | H |
| 34 | Me | H | Me | H | Me | COOH | H | H | H | H | Me | H |
| 35 | Me | H | Me | H | Me | COOH | H | H | H | H | Me | H |
| 36 | Me | SO$_3$H | Me | H | Me | COOH | H | H | H | H | Me | SO$_3$H |
| 37 | Me | H | Me | H | Me | CN | H | H | H | H | Me | H |
| 38 | Me | NMe$_2$ | Me | NMe$_2$ | Me | SO$_3$H | H | H | H | H | Me | NMe$_2$ |
| 39 | Me | NO$_2$ | Me | H | Me | SO$_3$H | H | H | H | H | Me | NO$_2$ |
| 40 | Me | SO$_3$H | Me | H | Me | H | H | H | H | Et | Me | SO$_3$H |
| 41 | H | SO$_3$H | H | NHCOMe | H | H | H | H | H | H | H | SO$_3$H |
| 42 | Me | NHCOiPr | Me | H | Me | H | H | H | H | H | Me | NHCOiPr |
| 43 | Me | NHCOMe | Me | NHCOMe | Me | SO$_3$H | H | H | H | H | Me | NHCOMe |
| 44 | Me | N(Et)COMe | Me | N(Et)COMe | Me | SO$_3$H | H | H | H | H | Me | N(Et)COMe |
| 45 | Me | NHCOiPr | Me | NHCOiPr | Me | SO$_3$H | H | H | H | H | Me | NHCOiPr |
| 46 | Me | NHCOC$_3$H$_6$COOH | Me | H | Me | H | H | H | H | H | Me | NHCOC$_3$H$_6$COOH |
| 47 | Me | NHCOiPr | Me | H | Me | SO$_3$H | H | H | H | H | Me | NHCOiPr |
| 48 | Me | NHCOiPr | Me | H | Me | SO$_3$H | H | H | H | H | Me | NHCOiPr |
| 49 | Me | NHCOCH(Et)Bu | Me | H | Me | SO$_3$H | H | H | H | H | Me | NHCOCH(Et)Bu |
| 50 | Me | NHCOC$_7$H$_{15}$ | Me | H | Me | SO$_3$H | H | H | H | H | Me | NHCOC$_7$H$_{15}$ |
| 51 | Me | NHCOC$_7$H$_{15}$ | Me | H | Me | SO$_3$H | H | H | H | H | Me | NHCOC$_7$H$_{15}$ |
| 52 | Me | NHCOC$_3$H$_6$COOH | Me | H | Me | SO$_3$H | H | H | H | H | Me | NHCOC$_3$H$_6$COOH |
| 53 | Me | NHCOiPr | Me | COMe | Me | SO$_3$H | H | H | H | H | Me | NHCOiPr |
| 54 | Me | NHCOC$_3$H$_6$COOH | Me | H | Me | SO$_3$H | H | H | H | H | Me | NHCOC$_3$H$_6$COOH |

| Exemplified Compounds | R$_{13}$ | R$_{14}$ | R$_{15}$ | R$_{16}$ | R$_{17}$ | R$_{18}$ | R$_{19}$ | R$_{20}$ | R$_{21}$ | R$_{22}$ | R$_{23}$ | R$_{24}$ |
|---|---|---|---|---|---|---|---|---|---|---|---|---|
| 28 | Me | H | Me | H | H | H | H | H | H | H | H | H |
| 29 | Me | H | Me | H | H | H | H | H | H | H | H | H |
| 30 | SO$_3$H | H | Me | Me | H | H | Me | H | H | H | H | H |
| 31 | Me | H | Me | NO$_2$ | H | H | H | H | H | H | H | H |
| 32 | Me | H | Me | Cl | H | H | H | H | H | SO$_3$H | H | H |
| 33 | Me | H | Me | Cl | H | H | H | H | H | H | H | H |
| 34 | Me | H | Me | COOH | H | H | H | H | H | H | H | H |
| 35 | Me | H | Me | COOH | H | H | H | H | H | SO$_3$H | H | H |
| 36 | Me | H | Me | COOH | H | H | H | H | H | H | H | H |
| 37 | Me | H | Me | CN | H | H | H | H | H | H | H | H |

TABLE 2-continued

Exemplified Compounds of Formula (1)

| 38 | Me | NMe$_2$ | Me | SO$_3$H | H | H | H | H | H | H | H | H |
|---|---|---|---|---|---|---|---|---|---|---|---|---|
| 39 | Me | H | Me | SO$_3$H | H | H | H | H | H | H | H | H |
| 40 | Me | H | Me | H | H | H | H | Et | H | H | H | H |
| 41 | H | NHCOMe | H | H | H | H | H | H | H | H | H | H |
| 42 | Me | H | Me | H | H | H | H | H | H | SO$_3$H | H | H |
| 43 | Me | NHCOMe | Me | SO$_3$H | H | H | H | H | H | H | H | H |
| 44 | Me | N(Et)COMe | Me | SO$_3$H | H | H | H | H | H | H | H | H |
| 45 | Me | NHCOiPr | Me | SO$_3$H | H | H | H | H | H | H | H | H |
| 46 | Me | H | Me | H | H | H | H | H | H | SO$_3$H | H | H |
| 47 | Me | H | Me | H | H | H | H | H | H | SO$_3$H | H | H |
| 48 | Me | H | Me | SO$_3$H | H | H | H | H | H | SO$_3$H | H | H |
| 49 | Me | H | Me | SO$_3$H | H | H | H | H | H | H | H | H |
| 50 | Me | H | Me | H | H | H | H | H | H | SO$_3$H | H | H |
| 51 | Me | H | Me | SO$_3$H | H | H | H | H | H | SO$_3$H | H | H |
| 52 | Me | H | Me | SO$_3$H | H | H | H | H | H | H | H | H |
| 53 | Me | COMe | Me | SO$_3$H | H | H | H | H | H | H | H | H |
| 54 | Me | H | Me | SO$_3$H | H | H | H | H | H | H | H | H |

Preparation of Ink

Components (unit: %) shown below were mixed and sufficiently stirred for dissolution, and then filtered under pressure using a filter having a pore size of 0.2 μm to prepare each ink. For all the compounds represented by Formula (1), sodium salt type compounds were used. Acetylenol E100 is a nonionic surfactant manufactured by Kawaken Fine Chemicals. Tables 3 and 4 show the content $C_1$ (%) of the compound represented by Formula (1) and the content $C_2$ (%) of the compound having a structure different from Formula (1). Moreover, Tables 3 and 4 also show a value of the mass ratio (times) of "Content $C_1$ (%) of compound represented by Formula (1) and Content $C_2$ (%) of compound having a structure different from Formula (1)". Coloring material (Types shown in Tables 3 and 4): Amount used (%) shown in Tables 3 and 4
Ethylene glycol: 9.00%
Diethylene glycol: 9.00%
Glycerol: 9.00%
Acetylenol E100: 0.50%
Ion exchanged water: Balance for 100.00% in total Components (unit: %) shown in Table 5 were mixed and sufficiently stirred for dissolution, and then filtered under pressure using a filter having a pore size of 0.45 μm to prepare each ink.

Coloring material (Types shown in Table 5): 3.50%
Ethylene glycol: 8.20%
Methanol: 27.60%
2-butanone: 27.60%
Chloroform: 27.60%.

The details of the other coloring materials are as shown below.

Triphenylmethane compound 1: C.I. Acid Blue 9
Triphenylmethane compound 2: C.I. Acid Blue 103
Triphenylmethane compound 3: Compound synthesized according to the above synthetic scheme 1 above
Triphenylmethane compound 4: C.I. Acid Blue 119
Phthalocyanine compound 1: Sodium salt type compound synthesized according to the synthetic method of Compound No. 1 of Japanese Patent Laid-Open No. 2004-323605
Phthalocyanine compound 2: Lithium salt type compound synthesized according to the synthetic method of Compound No. 154 of Japanese Patent Laid-Open No. 2003-231834
Phthalocyanine compound 3: Sodium salt type compound synthesized according to the synthetic method of Compound No. 1 of International Publication No. WO2010/119676

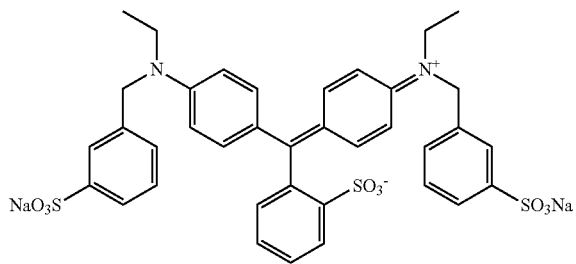

Triphenylmethane compound 1

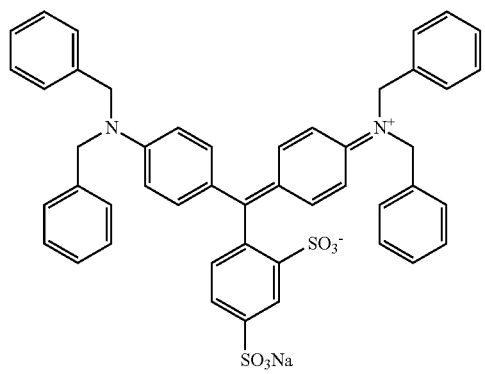

Triphenylmethane compound 2

-continued

Triphenylmethane compound 3

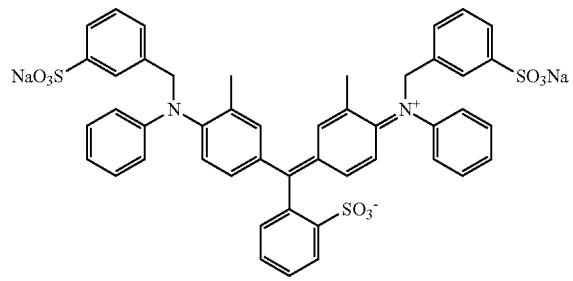

Triphenylmethane compound 4

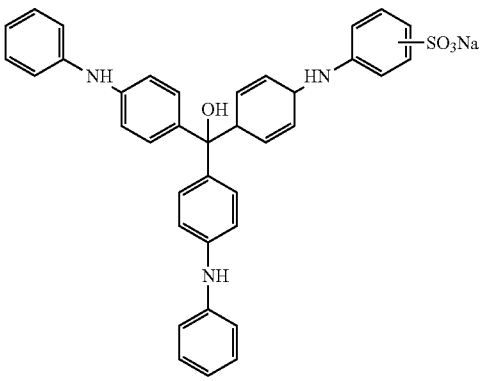

Phthalocyanine compound 1

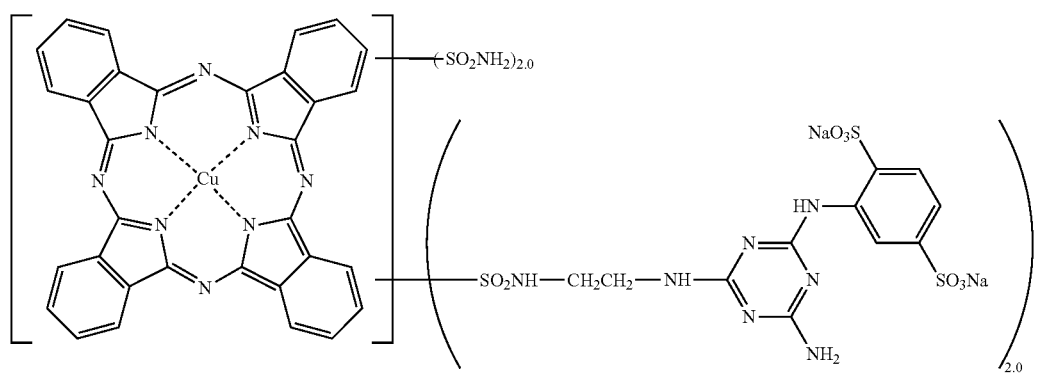

Phthalocyanine compound 2

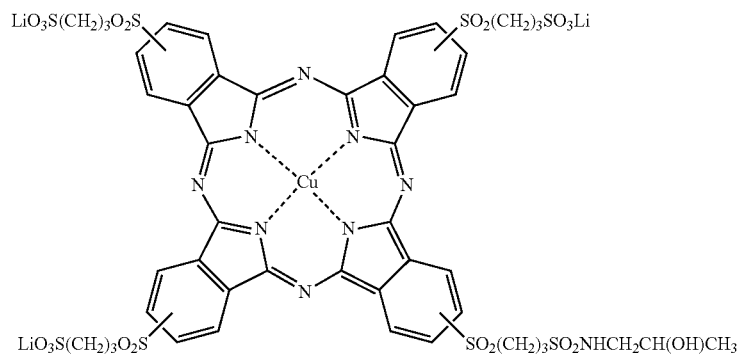

Phthalocyanine compound 4

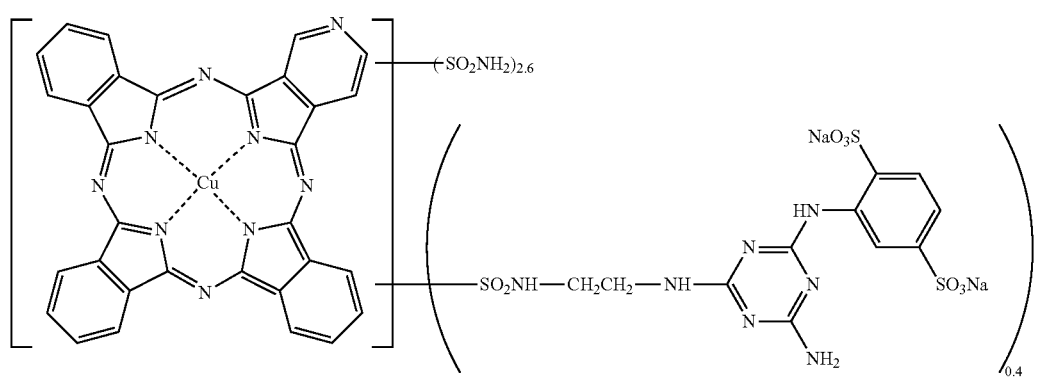

Evaluation

Inks having the compositions shown in Tables 3 and 4 each were filled into an ink cartridge, and then the ink cartridge was set in an ink jet recording apparatus (PIXUS iP8600; manufactured by CANON KABUSHIKI KAISHA) ejecting the ink from a recording head by the action of thermal energy. In this example, a solid image recorded by applying 8 ink droplets of 2.5 pL per ink droplet to a unit region to 1/600 inch×1/600 inch is defined as "Recording duty of 100%". Using the ink jet recording apparatus, a solid image with a recording duty of 100% was recorded on a glossy paper (CANON Photo Paper, Glossy Pro [Platinum Grade] PT-201; manufactured by CANON KABUSHIKI KAISHA) in an environment of a temperature of 23° C. and a relative humidity of 55% to obtain recorded matter. The obtained recorded matter was dried in an environment of a temperature of 23° C. and a relative humidity of 55% for 24 hours.

A solid image was recorded by applying each ink having the composition shown in Table 5 to a recording medium so that the ink application amount per unit region of 1 inch×1 inch was set to 7.37 µL in an environment of a temperature of 23° C. and a relative humidity of 55% to obtain recorded matter. As a recording medium, glossy paper (CANON Photo Paper, Glossy Pro [platinum grade] PT-201; manufactured by CANON KABUSHIKI KAISHA) was used. The application of the ink to the recording medium was performed by an RDS bar coater #5 (manufactured by R.D. Specialties). The obtained recorded matter was dried in an environment of a temperature of 23° C. and a relative humidity of 55% for 24 hours.

The following evaluations were performed using the recorded matter thus obtained. The colorimetry of images was performed under the conditions of Light source: D50 and Visual field: 20 using a spectrum photometer (Trade name "Spectorolino", manufactured by Gretag Macbeth). L*, a* and b* are L*, a* and b* in the L*a*b* display system specified by CIE (International Commission on Illumination). In the present disclosure, A and B are permissible levels and C and D are non-permissible levels in the evaluation criteria in the following evaluation items. The evaluation results are shown in Tables 3 to 5.

Color Developability

The solid image portion of the recorded matter recorded using the inks having the compositions shown in Tables 3 to 5 was measured for optical density. From the obtained optical density values, the color developability was evaluated in accordance with the evaluation criteria shown below.
A: Optical density was 2.40 or more.
B: Optical density was 2.30 or more to less than 2.40.
C: Optical density was 2.20 or more to less than 2.30.

Ozone Resistance

The solid image portion of the recorded matter recorded using the inks having the compositions shown in Tables 3 to 5 was measured for optical density (which was defined as "optical density before test"). Thereafter, the recorded matter was placed in an ozone weather meter (OMS-H, manufactured by Suga Test Instruments), and then the solid image was exposed to ozone for 24 hours under the conditions of a temperature in the chamber of 23° C., a relative humidity of 50%, and an ozone concentration of 10 ppm. Subsequently, the solid image portion of the recorded matter was measured for optical density (which was defined as "optical density after test"). Then, Optical density residual ratio (%)=(Optical density after test/Optical density before test)×100 was calculated, and then the ozone resistance was evaluated in accordance with the evaluation criteria shown below.
A: The optical density residual ratio was 70% or more.
B: The optical density residual ratio was 40% or more to less than 70%.
C: The optical density residual ratio was 10% or more to less than 40%.
D: The optical density residual ratio was less than 10%.

Light Fastness

The solid image portion of the recorded matter recorded using the inks having the compositions shown in Tables 3 to 5 was measured for optical density (which was defined as "optical density before test"). Thereafter, the recorded matter was placed in a super xenon test device (SX-120; manufactured by Suga Test Instruments), and then the solid image was irradiated with xenon light for 70 hours under the conditions of a temperature in the chamber of 24° C., a relative humidity of 60% and illuminance of 150 klx. Subsequently, the solid image portion of the recorded matter was measured for optical density (which was defined as "optical density after test"). Then, Optical density residual ratio (%)=(Optical density after test/Optical density before test)×100 was calculated, and then the light fastness was evaluated in accordance with the evaluation criteria shown below.
A: The optical density residual ratio was 70% or more.
B: The optical density residual ratio was 45% or more to less than 70%.
C: The optical density residual ratio was 20% or more to less than 45%.
D: The optical density residual ratio was less than 20%.

Moisture Resistance

Using the inks having the compositions shown in Tables 3 and 4 and the same ink jet recording apparatus as above, an image of the following pattern was recorded on a glossy paper (CANON Photo Paper, Glossy Gold GL-101; manufactured by CANON KABUSHIKI KAISHA) in an environment of a temperature of 23° C. and a relative humidity of 55% to obtain recorded matter. The pattern is a pattern in which a solid image with a recording duty of 100% and a non-recording portion of the same size as the size of the solid image are disposed in the shape of a lattice. The obtained recorded matter was dried in an environment of a temperature of 23° C. and a relative humidity of 55% for 24 hours. Then, the solid image portion in the recorded matter was measured for L*, a* and b* (which were defined as $L_1^*$, $a_1^*$ and $b_1^*$) Thereafter, the recorded matter was placed in a thermohygrostat of a temperature of 30° C. and a relative humidity of 90% for 168 hours. Subsequently, the solid image portion of the recorded matter was measured for L*, a* and b* (which was defined as $L_2^*$, $a_2^*$ and $b_2^*$). Then, a color change $(\Delta E)=\{(L_1^*-L_2^*)^2+(a_1^*-a_2^*)^2+(b_1^*-b_2^*)^2\}^{1/2}$ was calculated, and then the moisture resistance was evaluated in accordance with the evaluation criteria shown below.
A: ΔE was less than 5.
B: ΔE was 5 or more to less than 15.
C: ΔE was 15 or more to less than 25.
D: ΔE was 25 or more.

TABLE 3

Compositions, properties and evaluation results of inks

| | | Composition of ink | | | Property of ink | | Mass ratio | Evaluation results | | | |
|---|---|---|---|---|---|---|---|---|---|---|---|
| | | Compound represented by Formula (1) | Amount used (%) | Other coloring materials | Amount used (%) | Content $C_1$ (%) | Content $C_2$ (%) | $C_1/C_2$ (times) | Color developability | Ozone resistance | Light fastness | Moisture resistance |
| Examples | 1 | Exemplified compound 1 | 3.50 | — | — | 3.50 | 0.00 | — | B | B | A | B |
| | 2 | Exemplified compound 2 | 3.50 | — | — | 3.50 | 0.00 | — | B | A | A | B |
| | 3 | Exemplified compound 3 | 3.50 | — | — | 3.50 | 0.00 | — | B | A | A | B |
| | 4 | Exemplified compound 4 | 3.50 | — | — | 3.50 | 0.00 | — | B | A | A | B |
| | 5 | Exemplified compound 5 | 3.50 | — | — | 3.50 | 0.00 | — | B | A | A | B |
| | 6 | Exemplified compound 6 | 3.50 | — | — | 3.50 | 0.00 | — | B | A | A | B |
| | 7 | Exemplified compound 7 | 3.50 | — | — | 3.50 | 0.00 | — | B | A | A | B |
| | 8 | Exemplified compound 8 | 3.50 | — | — | 3.50 | 0.00 | — | B | A | A | B |
| | 9 | Exemplified compound 9 | 3.50 | — | — | 3.50 | 0.00 | — | B | A | A | B |
| | 10 | Exemplified compound 10 | 3.50 | — | — | 3.50 | 0.00 | — | B | A | A | B |
| | 11 | Exemplified compound 11 | 3.50 | — | — | 3.50 | 0.00 | — | B | A | A | B |
| | 12 | Exemplified compound 12 | 3.50 | — | — | 3.50 | 0.00 | — | A | A | B | B |
| | 13 | Exemplified compound 13 | 3.50 | — | — | 3.50 | 0.00 | — | B | A | B | B |
| | 14 | Exemplified compound 14 | 3.50 | — | — | 3.50 | 0.00 | — | B | A | B | B |
| | 15 | Exemplified compound 15 | 3.50 | — | — | 3.50 | 0.00 | — | B | A | B | B |
| | 16 | Exemplified compound 16 | 3.50 | — | — | 3.50 | 0.00 | — | A | A | A | A |
| | 17 | Exemplified compound 17 | 3.50 | — | — | 3.50 | 0.00 | — | B | A | A | A |
| | 18 | Exemplified compound 18 | 3.50 | — | — | 3.50 | 0.00 | — | B | B | A | A |
| | 19 | Exemplified compound 19 | 3.50 | — | — | 3.50 | 0.00 | — | B | B | A | A |
| | 20 | Exemplified compound 20 | 3.50 | — | — | 3.50 | 0.00 | — | A | B | A | A |
| | 21 | Exemplified compound 21 | 3.50 | — | — | 3.50 | 0.00 | — | B | B | A | A |
| | 22 | Exemplified compound 22 | 3.50 | — | — | 3.50 | 0.00 | — | A | B | A | A |
| | 23 | Exemplified compound 23 | 3.50 | — | — | 3.50 | 0.00 | — | A | A | A | A |
| | 24 | Exemplified compound 24 | 3.50 | — | — | 3.50 | 0.00 | — | A | A | A | A |
| | 25 | Exemplified compound 25 | 3.50 | — | — | 3.50 | 0.00 | — | A | A | A | A |
| | 26 | Exemplified compound 26 | 3.50 | — | — | 3.50 | 0.00 | — | B | A | A | A |
| | 27 | Exemplified compound 27 | 3.50 | — | — | 3.50 | 0.00 | — | B | A | A | A |
| | 28 | Exemplified compound 29 | 3.50 | — | — | 3.50 | 0.00 | — | A | A | A | A |
| | 29 | Exemplified compound 30 | 3.50 | — | — | 3.50 | 0.00 | — | B | A | A | A |
| | 30 | Exemplified compound 31 | 3.50 | — | — | 3.50 | 0.00 | — | A | A | A | A |
| | 31 | Exemplified compound 32 | 3.50 | — | — | 3.50 | 0.00 | — | A | A | A | A |
| | 32 | Exemplified compound 34 | 3.50 | — | — | 3.50 | 0.00 | — | A | A | A | A |
| | 33 | Exemplified compound 35 | 3.50 | — | — | 3.50 | 0.00 | — | A | A | A | A |
| | 34 | Exemplified compound 36 | 3.50 | — | — | 3.50 | 0.00 | — | A | A | A | A |

TABLE 3-continued

Compositions, properties and evaluation results of inks

| | Composition of ink | | | | Property of ink | | Mass ratio $C_1/C_2$ (times) | Evaluation results | | | |
|---|---|---|---|---|---|---|---|---|---|---|---|
| | Compound represented by Formula (1) | Amount used (%) | Other coloring materials | Amount used (%) | Content $C_1$ (%) | Content $C_2$ (%) | | Color developability | Ozone resistance | Light fastness | Moisture resistance |
| 35 | Exemplified compound 38 | 3.50 | — | — | 3.50 | 0.00 | — | A | A | A | A |
| 36 | Exemplified compound 39 | 3.50 | — | — | 3.50 | 0.00 | — | A | A | A | A |
| 37 | Exemplified compound 40 | 3.50 | — | — | 3.50 | 0.00 | — | A | A | A | A |
| 38 | Exemplified compound 41 | 3.50 | — | — | 3.50 | 0.00 | — | B | A | A | A |
| 39 | Exemplified compound 42 | 3.50 | — | — | 3.50 | 0.00 | — | A | B | A | A |

TABLE 4

Compositions, properties and evaluation results of inks

| | | Composition of ink | | | | Property of ink | | Mass ratio $C_1/C_2$ (times) | Evaluation results | | | |
|---|---|---|---|---|---|---|---|---|---|---|---|---|
| | | Compound represented by Formula (1) | Amount used (%) | Other coloring materials | Amount used (%) | Content $C_1$ (%) | Content $C_2$ (%) | | Color developability | Ozone resistance | Light fastness | Moisture resistance |
| Examples | 40 | Exemplified compound 43 | 3.50 | — | — | 3.50 | 0.00 | — | A | A | A | A |
| | 41 | Exemplified compound 44 | 3.50 | — | — | 3.50 | 0.00 | — | A | A | A | A |
| | 42 | Exemplified compound 45 | 3.50 | — | — | 3.50 | 0.00 | — | A | A | A | A |
| | 43 | Exemplified compound 46 | 3.50 | — | — | 3.50 | 0.00 | — | A | B | A | A |
| | 44 | Exemplified compound 47 | 3.50 | — | — | 3.50 | 0.00 | — | A | A | A | A |
| | 45 | Exemplified compound 48 | 3.50 | — | — | 3.50 | 0.00 | — | A | A | A | A |
| | 46 | Exemplified compound 49 | 3.50 | — | — | 3.50 | 0.00 | — | A | A | A | A |
| | 47 | Exemplified compound 50 | 3.50 | — | — | 3.50 | 0.00 | — | A | A | A | A |
| | 48 | Exemplified compound 51 | 3.50 | — | — | 3.50 | 0.00 | — | A | A | A | A |
| | 49 | Exemplified compound 52 | 3.50 | — | — | 3.50 | 0.00 | — | A | A | A | A |
| | 50 | Exemplified compound 53 | 3.50 | — | — | 3.50 | 0.00 | — | A | A | A | A |
| | 51 | Exemplified compound 54 | 3.50 | — | — | 3.50 | 0.00 | — | A | A | A | A |
| | 52 | Exemplified compound 42 | 1.75 | Triphenylmethane compound 1 | 1.75 | 1.75 | 1.75 | 1.00 | A | A | A | A |
| | 53 | Exemplified compound 42 | 1.75 | Phthalocyanine compound 1 | 1.75 | 1.75 | 1.75 | 1.00 | A | A | A | A |
| | 54 | Exemplified compound 42 | 1.75 | Phthalocyanine compound 2 | 1.75 | 1.75 | 1.75 | 1.00 | A | A | A | A |
| | 55 | Exemplified compound 42 | 1.75 | Phthalocyanine compound 3 | 1.75 | 1.75 | 1.75 | 1.00 | A | A | A | A |
| | 56 | Exemplified compound 10 | 1.75 | Phthalocyanine compound 3 | 1.75 | 1.75 | 1.75 | 1.00 | B | A | A | A |
| | 57 | Exemplified compound 13 | 1.75 | Phthalocyanine compound 3 | 1.75 | 1.75 | 1.75 | 1.00 | B | A | A | A |
| | 58 | Exemplified compound 46 | 1.75 | Phthalocyanine compound 3 | 1.75 | 1.75 | 1.75 | 1.00 | A | A | A | A |
| | 59 | Exemplified compound 46 | 0.20 | Phthalocyanine compound 3 | 3.30 | 0.20 | 3.30 | 0.06 | A | A | A | A |
| | 60 | Exemplified compound 46 | 1.75 | Phthalocyanine compound 3 | 0.50 | 3.00 | 0.50 | 6.00 | A | A | A | A |

TABLE 4-continued

Compositions, properties and evaluation results of inks

| | | Composition of ink | | | | Property of ink | | | Evaluation results | | | |
|---|---|---|---|---|---|---|---|---|---|---|---|---|
| | | Compound represented by Formula (1) | Amount used (%) | Other coloring materials | Amount used (%) | Content $C_1$ (%) | Content $C_2$ (%) | Mass ratio $C_1/C_2$ (times) | Color developability | Ozone resistance | Light fastness | Moisture resistance |
| | 61 | Exemplified compound 46 | 0.15 | Phthalocyanine compound 3 | 3.35 | 0.15 | 3.35 | 0.04 | A | A | A | A |
| | 62 | Exemplified compound 46 | 3.05 | Phthalocyanine compound 3 | 0.45 | 3.05 | 0.45 | 6.78 | A | A | A | A |
| Comparative Examples | 1 | — | — | Triphenylmethane compound 1 | 3.50 | 0.00 | 3.50 | 0.00 | A | D | D | D |
| | 2 | — | — | Triphenylmethane compound 2 | 3.50 | 0.00 | 3.50 | 0.00 | A | B | D | C |
| | 3 | — | — | Triphenylmethane compound 3 | 3.50 | 0.00 | 3.50 | 0.00 | B | D | C | B |
| | 4 | — | — | Triphenylmethane compound 4 | 3.50 | 0.00 | 3.50 | 0.00 | B | D | D | B |
| | 5 | — | — | Phthalocyanine compound 1 | 3.50 | 0.00 | 3.50 | 0.00 | C | C | C | A |
| | 6 | — | — | Phthalocyanine compound 2 | 3.50 | 0.00 | 3.50 | 0.00 | C | B | B | A |
| | 7 | — | — | Phthalocyanine compound 3 | 3.50 | 0.00 | 3.50 | 0.00 | C | A | A | A |
| | 8 | — | — | Triphenylmethane compound 1 Phthalocyanine compound 3 | 1.75 1.75 | 0.00 | 3.50 | 0.00 | A | C | C | C |
| | 9 | — | — | Triphenylmethane compound 2 Phthalocyanine compound 3 | 1.75 1.75 | 0.00 | 3.50 | 0.00 | A | B | C | C |
| | 10 | — | — | Triphenylmethane compound 3 Phthalocyanine compound 3 | 1.75 1.75 | 0.00 | 3.50 | 0.00 | A | C | B | C |
| | 11 | — | — | Triphenylmethane compound 4 Phthalocyanine compound 3 | 1.75 1.75 | 0.00 | 3.50 | 0.00 | B | C | C | C |

TABLE 5

Compositions and evaluation results of inks

| | | Composition of ink | | Evaluation results | | |
|---|---|---|---|---|---|---|
| | | Compound represented by Formula (1) | Other coloring materials | Color developability | Ozone resistance | Light fastness |
| Examples | 63 | Exemplified Compound 12 | — | A | A | B |
| | 64 | Exemplified Compound 18 | — | B | B | A |
| | 65 | Exemplified Compound 20 | — | A | B | A |
| | 66 | Exemplified Compound 28 | — | B | B | A |
| | 67 | Exemplified Compound 33 | — | B | A | A |
| | 68 | Exemplified Compound 37 | — | B | A | A |
| | 69 | Exemplified Compound 42 | — | A | B | A |
| Comparative Examples | 12 | — | Triphenylmethane compound 1 | A | D | D |
| | 13 | — | Phthalocyanine compound 3 | C | A | A |

The evaluation results of the "color developability" of Examples 59 and 61 were all "A" but Example 59 was relatively superior to Example 61. The evaluation results of the "ozone resistance" of Examples 60 and 62 were all "A" but Example 60 was relatively superior to Example 62.

A compound having high color developability and excellent also in ozone resistance, light fastness and moisture resistance and useful as a coloring material can be provided. According to another embodiment of the present disclosure, an ink containing the coloring material, an ink cartridge containing the ink and an ink jet recording method can be provided.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-038353 filed Feb. 29, 2016 and No. 2017-013676 filed Jan. 27, 2017, which are hereby incorporated by reference herein in their entirety.

What is claimed is:

1. A compound represented by the following formula (1),

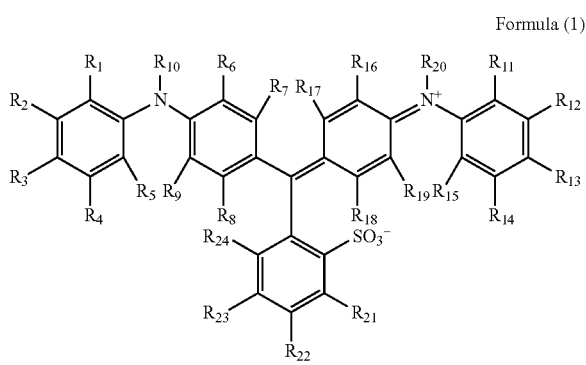

Formula (1)

wherein, in Formula (1), $R_1$ to $R_{24}$ each independently represent a hydrogen atom, a halogen atom, an alkyl group, a cycloalkyl group, an alkenyl group, an alkynyl group, an aryl group, an aralkyl group, an acyl group, an acylamino group, a sulfonylamino group, an alkoxy group, an aryloxy group, a hydroxy group, an amino group, a nitro group, a cyano group, a sulfonic acid group, a carboxylic acid group, a sulfamoyl group, a carbamoyl group, an alkoxysulfonyl group, an alkoxycarbonyl group, an aryloxysulfonyl group or an aryloxycarbonyl group and satisfy at least one of (X) and (Y) below: (X) at least one of $R_1$ to $R_{24}$ is a sulfonic acid group or a carboxylic acid group; (Y) at least one of $R_6$, $R_7$, $R_8$, $R_9$, $R_{16}$, $R_{17}$, $R_{18}$ and $R_{19}$ is a halogen atom, an acyl group, a nitro group or a cyano group.

2. The compound according to claim 1, wherein a number of $R_1$ to $R_{24}$ in Formula (1) which represent a halogen atom, an acyl group, a nitro group, a cyano group, a sulfonic acid group and a carboxylic acid group is 2 or more to 5 or less.

3. The compound according to claim 1, wherein at least one of $R_6$, $R_7$, $R_8$, $R_9$, $R_{16}$, $R_{17}$, $R_{18}$ and $R_{19}$ in Formula (1) is a sulfonic acid group or a carboxylic acid group.

4. The compound according to claim 1, wherein at least two of $R_1$, $R_2$, $R_3$, $R_4$, $R_5$, $R_{11}$, $R_{12}$, $R_{13}$, $R_{14}$ and $R_{15}$ in Formula (1) each independently represent an alkyl group or an acylamino group.

5. The compound according to claim 1, wherein $R_1$, $R_5$, $R_{11}$ and $R_{15}$ in Formula (1) each independently represent an alkyl group.

6. The compound according to claim 1, wherein at least one of $R_2$ and $R_4$ in Formula (1) and at least one of $R_{12}$ and $R_{14}$ each independently represent an acylamino group.

7. The compound according to claim 1, wherein at least one of $R_{10}$ and $R_{20}$ in Formula (1) is a hydrogen atom.

8. The compound according to claim 1, wherein $R_1$ and $R_{11}$, $R_2$ and $R_{12}$, $R_3$ and $R_{13}$, $R_4$ and $R_{14}$, $R_5$ and $R_{15}$, $R_6$ and $R_{16}$, $R_7$ and $R_{17}$, $R_8$ and $R_{18}$, and $R_9$ and $R_{19}$ in Formula (1) each independently represent a same group.

9. An ink comprising:

a coloring material, wherein the coloring material contains a compound represented by the following formula (1),

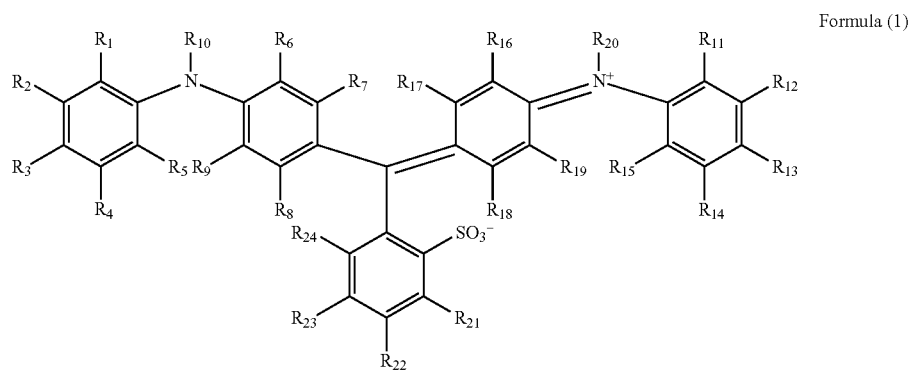

Formula (1)

wherein, in Formula (1), $R_1$ to $R_{24}$ each independently represent a hydrogen atom, a halogen atom, an alkyl group, a cycloalkyl group, an alkenyl group, an alkynyl group, an aryl group, an aralkyl group, an acyl group, an acylamino group, a sulfonylamino group, an alkoxy group, an aryloxy group, a hydroxy group, an amino group, a nitro group, a cyano group, a sulfonic acid group, a carboxylic acid group, a sulfamoyl group, a carbamoyl group, an alkoxysulfonyl group, an alkoxycarbonyl group, an aryloxysulfonyl group or an aryloxycarbonyl group and satisfy at least one of (X) and (Y) below: (X) at least one of $R_1$ to $R_{24}$ is a sulfonic acid group or a carboxylic acid group; (Y) at least one of $R_6$, $R_7$, $R_8$, $R_9$, $R_{16}$, $R_{17}$, $R_{18}$ and $R_{19}$ is a halogen atom, an acyl group, a nitro group or a cyano group.

10. The ink according to claim 9, wherein the coloring material further contains a compound having a different structure from that of the compound represented by the Formula (1).

11. The ink according to claim 9, wherein the ink is an ink jet ink.

12. An ink cartridge comprising:

an ink; and an ink storage portion storing the ink, wherein the ink comprises the ink according to claim 9.

13. An ink jet recording method comprising:
ejecting an ink from a recording head of an ink jet system to record an image on a recording medium,
wherein the ink comprises the ink according to claim 9.

* * * * *